US008703056B2

(12) United States Patent
Sakairi et al.

(10) Patent No.: US 8,703,056 B2
(45) Date of Patent: Apr. 22, 2014

(54) AUTOMATED ANALYZER AND DEVICE FOR OPENING/CLOSING THE LIDS OF REAGENT VESSELS

(75) Inventors: Susumu Sakairi, Hitachinaka (JP);
Katsuaki Takahashi, Hitachinaka (JP);
Stephan Sattler, Mannheim (DE);
Reinhold Kraemer, Mannheim (DE)

(73) Assignees: Hitachi High-Technologies Corporation, Tokyo (JP); F. Hoffman-La Roche AG, Basel (CH)

( * ) Notice: Subject to any disclaimer, the term of this patent is extended or adjusted under 35 U.S.C. 154(b) by 0 days.

(21) Appl. No.: 13/515,580

(22) PCT Filed: Dec. 9, 2010

(86) PCT No.: PCT/JP2010/072128
§ 371 (c)(1),
(2), (4) Date: Aug. 20, 2012

(87) PCT Pub. No.: WO2011/074472
PCT Pub. Date: Jun. 23, 2011

(65) Prior Publication Data
US 2012/0328475 A1    Dec. 27, 2012

(30) Foreign Application Priority Data

Dec. 14, 2009    (JP) .................................. 2009-282889

(51) Int. Cl.
G01N 21/00    (2006.01)
G01N 31/00    (2006.01)
G01N 33/00    (2006.01)

(52) U.S. Cl.
USPC .................... 422/67; 422/63; 422/64; 422/65

(58) Field of Classification Search
None
See application file for complete search history.

(56) References Cited

U.S. PATENT DOCUMENTS

| 4,495,149 A * | 1/1985 | Iwata et al. ...................... 422/65 |
| 5,358,691 A * | 10/1994 | Clark et al. ...................... 422/64 |
| 5,628,962 A * | 5/1997 | Kanbara et al. .................. 422/63 |
| 6,531,096 B1 * | 3/2003 | Deveney et al. ................. 422/65 |
| 6,890,485 B1 * | 5/2005 | Stylli et al. ...................... 506/39 |
| 2001/0028863 A1 * | 10/2001 | Kitagawa ...................... 422/100 |

FOREIGN PATENT DOCUMENTS

| JP | 64-061667 A | 3/1989 |
| JP | 08-094624 A | 4/1996 |
| JP | 2955613 B2 | 7/1999 |
| JP | 2001-343392 A | 12/2001 |
| JP | 2009-109403 A | 5/2009 |

* cited by examiner

Primary Examiner — Jill Warden
Assistant Examiner — Brittany Fisher
(74) Attorney, Agent, or Firm — Mattingly & Malur, PC

(57) ABSTRACT

An automated analyzer and a reagent vessel opening/closing device allows reduction of the time period during which reagent vessels are opened unnecessarily. The reagent vessel opening/closing device opens or closes the lids of reagent vessels when the reagent vessels are at a dispensing/stirring position on a reagent vessel transfer device of an automated analyzer. The device for opening/closing the lids of reagent vessels includes a hook base secured to a unit base and a hook-base drive unit for moving the hook base with respect to the unit base in opening/closing directions of the lids of the reagent vessels. A plurality of hooks are attached to the hook base and a plurality of motors are each adapted to slide one of the hooks with respect to the hook base to engage/disengage the hook with/from the lid of a reagent vessel.

10 Claims, 22 Drawing Sheets

AUTOMATED ANALYZER AND DEVICE FOR OPENING/CLOSING THE LIDS OF REAGENT VESSELS

TECHNICAL FIELD

The present invention relates to an automated analyzer for performing biochemical analysis in a clinical setting or chemical analysis such as immunoassays and the like and particularly to a device for opening or closing the lids of reagent vessels.

BACKGROUND ART

During an immunoassay or the like, an analyte (a substance to be analyzed) is measured quantitatively by analyzing an antigen-antibody reaction. This is typically done by the following procedure. First, a sample containing the analyte is mixed with magnetic particles, an antibody including a labeled substance, and an antibody that binds the magnetic particles to the analyte, thereby causing an antigen-antibody reaction. Then, a magnetic separator is used to capture the resultant substance formed by the binding between the analyte, the magnetic particles, and the labeled substance. Thereafter, a voltage is applied to the captured substance to measure its luminescence value. Such a chemical analysis often requires the use of an automated analyzer.

An example of such an automated analyzer is the one disclosed in Japanese Patent No. 2955613 (Patent Document 1). This automated analyzer uses one set of reagent vessels for each sample analysis. One reagent vessel set consists of three reagent vessels: a vessel that contains a solution including magnetic particles; a vessel that contains a solution including a labeled substance; and a vessel that contains a solution including an antibody. Each of the reagent vessels has a lid so as to prevent reagent evaporation or deterioration.

PRIOR ART LITERATURE

[Patent Document 1] Japanese Patent No. 2955613

SUMMARY OF THE INVENTION

Problem to be Solved by the Invention

The device for opening/closing the lids of reagent vessels of Patent Document 1 is capable of simultaneously opening or closing up to three lids of a reagent vessel set. However, this reagent vessel opening/closing device is not capable of opening or closing the second and third vessels of that set without opening or closing its first vessel, which is closest to the device for opening/closing the lids of reagent vessels. In other words, the second vessel has to be opened or closed at the same as the first vessel, and the third vessel has to be opened or closed at the same as the first and second vessels. Thus, when only the third vessel need be opened, the first and second vessels that need not be opened have to be opened as well. For this reason, conventional reagent vessel opening/closing devices have room for improvement in preventing reagent evaporation or deterioration.

In view of the above, an object of the invention is thus to provide an automated analyzer and a reagent vessel opening/closing device that allow reduction of the time period during which reagent vessels are opened unnecessarily.

Means for Solving the Problem

The automated analyzer of the invention selectively opens or closes the lids of reagent vessels. This selective lid opening or closing is achieved by 1) attaching multiple hooks to a hook base, 2) providing hook drive mechanisms inside the hook base to individually engage/disengage the hooks with/from the lids, and 3) moving the hook base in opening/closing directions of the lids with the use of a hook-base drive unit.

Effect of the Invention

In accordance with the invention, it is possible to reduce the time period during which reagent vessels are opened unnecessarily and prevent reagent evaporation or deterioration.

MODE FOR CARRYING OUT THE INVENTION

Embodiments of the present invention will now be described with reference to the accompanying drawings.

Figure 1:
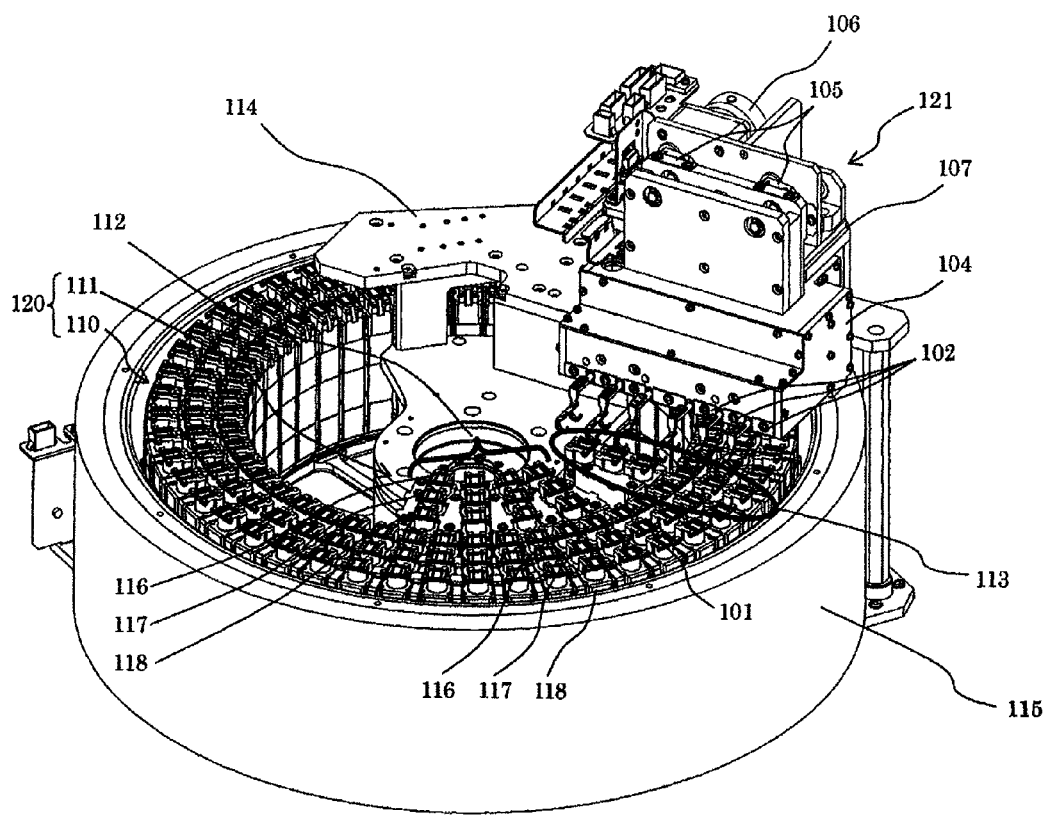
FIG. 1 is a perspective view illustrating part of an automated analyzer with a reagent vessel opening/closing device according to an embodiment of the invention.
Figure 2:
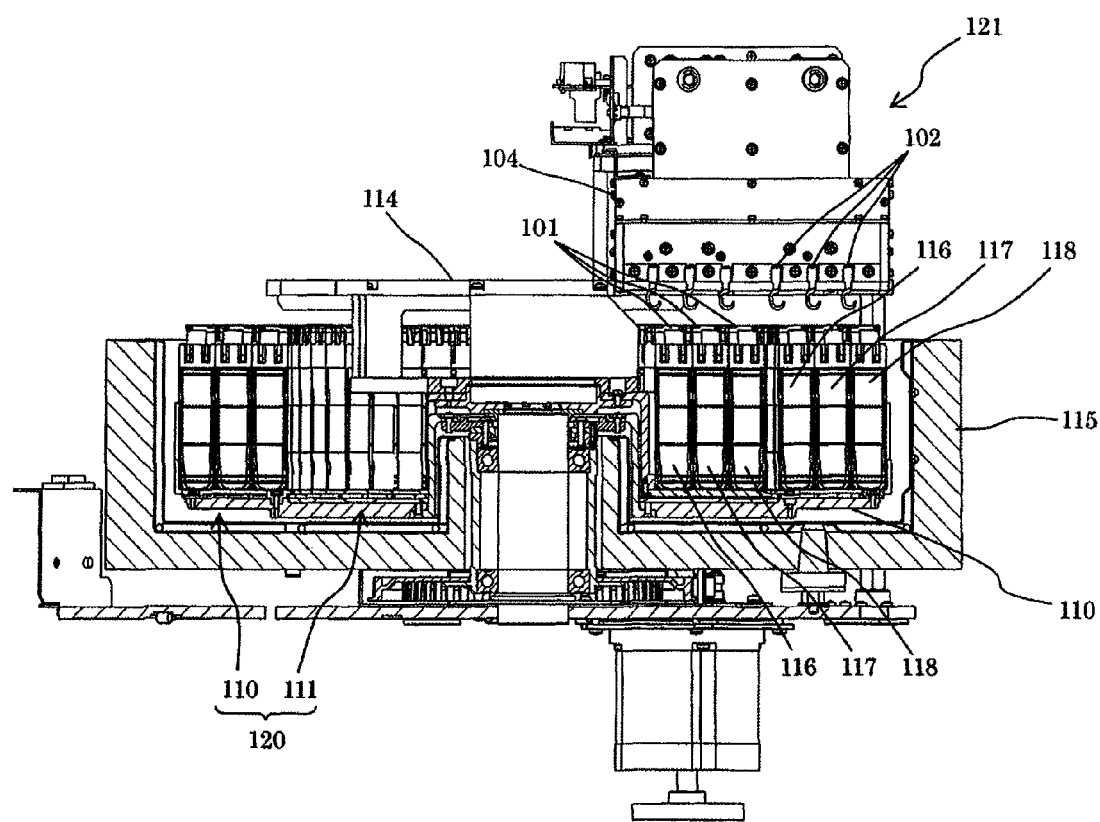
FIG. 2 is a cross-section of the device for opening/closing the lids of reagent vessels taken at the reagent dispensing/stirring position of the analyzer.

FIG. 1 is a perspective view illustrating part of an automated analyzer with a reagent vessel opening/closing device according to an embodiment of the invention, and FIG. 2 is a cross-section of the device for opening/closing the lids of reagent vessels taken at the reagent dispensing/stirring position of the analyzer.

The automated analyzer of FIGS. 1 and 2 is designed to automatically perform biochemical analysis in a clinical setting or chemical analysis such as immunoassays and the like. In the explanation that follows, we assume that the automated analyzer uses magnetic-particle reagents for analysis of samples, but other types of reagent are also applicable.

The automated analyzer includes a reagent disk 120 (i.e., reagent vessel transfer device) and the device for opening/closing the lids of reagent vessels, which is indicated by reference numeral 121. The reagent disk 120 allows placement of multiple sets of reagent vessels, wherein each set consists of three reagent vessels 116, 117, and 118 that each contain a reagent for analysis of a sample. When a particular set of reagent vessels 116 to 118 lies at a dispensing/stirring position 113 on the reagent disk 120, the device for opening/closing the lids of reagent vessels 121 opens or closes particular lids 101 of those reagent vessels 116 to 118.

All the reagent vessel sets are arranged on the reagent disk 120 in a radial manner. The reagent disk 120 comprises an outer disk 110 and an inner disk 111. The outer disk 110 is allowed to rotate horizontally around a vertical axis whereas the inner disk 111 is fixed to the reagent disk 120. The inner disk 111 has a standby position 112 at which some sets of reagent vessels 116 to 118 are placed as standbys and includes part of the aforementioned dispensing/stirring position 113 at which a reagent is dispensed or stirred. As illustrated by the circle of FIG. 1, the dispensing/stirring position 113 allows placement of two sets of reagent vessels 116 to 118, with one set placed on the inner disk 111 and the other placed on the outer disk 110. At the dispensing/stirring position 113, a reagent vessel transfer mechanism (not illustrated) transfers a reagent vessel set from the outer disk 110 to the inner disk 111 or vice versa for analysis. A frame 114 is positioned over the reagent disk 120 so as to cover the outer disk 110 and the inner disk 111. The device for opening/closing the lids of reagent vessels 121 is secured to the frame 114 such that the device for opening/closing the lids of reagent vessels 121 is located right above the dispensing/stirring position 113.

The following is a possible scenario in which the automated analyzer performs an analysis. Assume that a reagent vessel set contains three different reagents, with a reagent vessel 116 containing a magnetic-particle reagent and reagent vessels 117 and 118 containing mutually different reagents A and B, respectively. In that case, at least one of the reagents A and B is first mixed with a sample and heated for a given amount of time to facilitate reaction. As necessary, the magnetic-particle reagent is thereafter mixed with the reagent(s) that has (have) been mixed with the sample and then heated further. The automated analyzer then analyzes the resultant liquid, using a subsequent-stage analysis mechanism (not illustrated). Of course, the order of reagent mixing or the heating time may vary, depending on attributes to be analyzed. Also, sample dilution or removing an undesired component from the resultant liquid before measuring may be performed as necessary.

Figure 3:
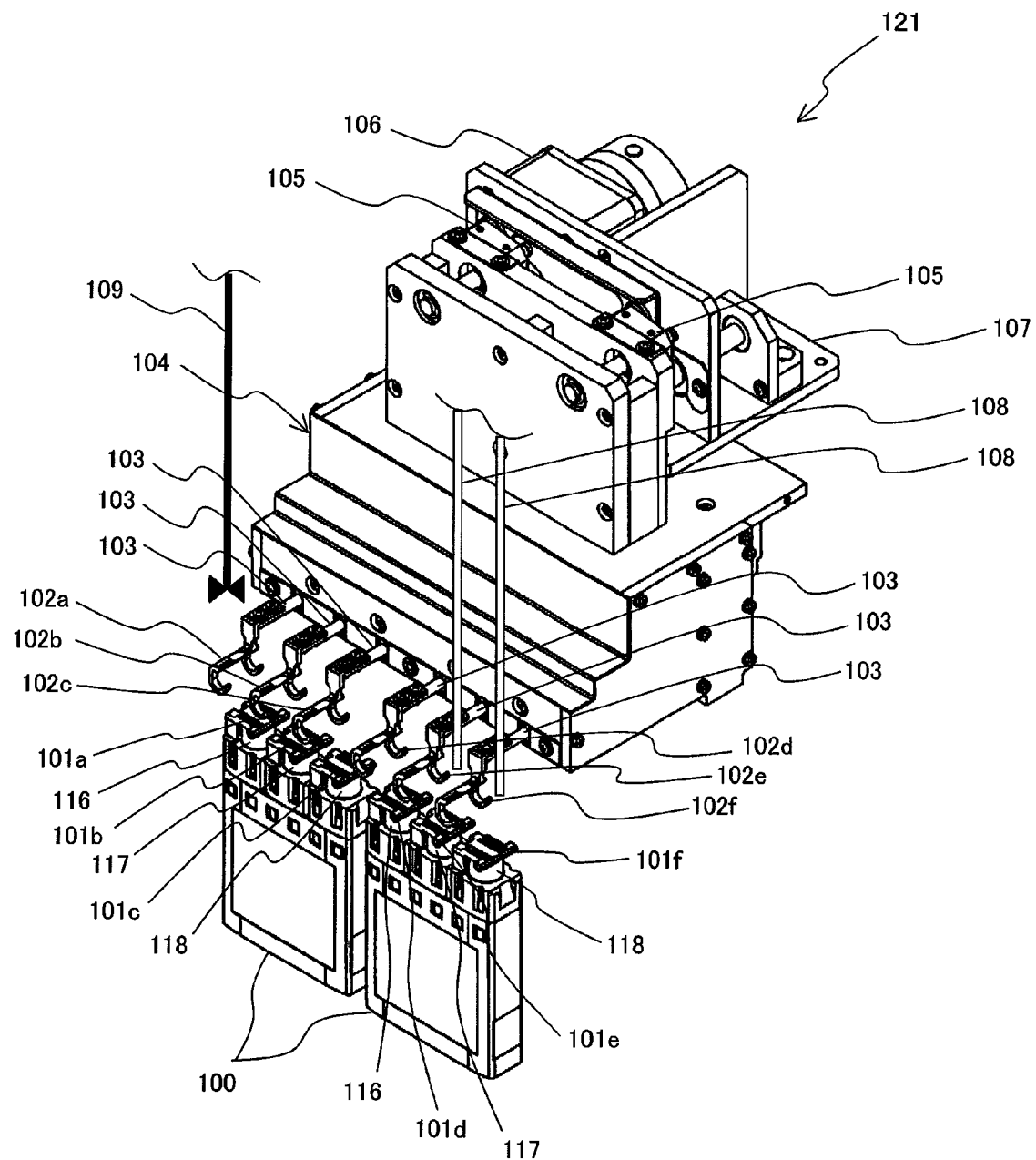
FIG. 3 is a perspective view of the device for opening/closing the lids of reagent vessels.

As illustrated in FIG. 3, reagent suctioning probes 108 used to dispense reagents are capable of accessing particular ones of the reagent vessels 116 to 118 in a container 100 located on the outer disk 110. A reagent stirring rod 109 used to stir a reagent, on the other hand, is capable of accessing a particular one of the reagent vessels 116 to 118 in a container 100 located on the inner disk 111. The outer-disk-110 side of the dispensing/stirring position 113 is the position at which, for the purpose of dispensing reagents, the reagent suctioning probes 108 access particular ones of the reagent vessels 116 to 118 that lie at that position. The inner-disk-111 side of the dispensing/stirring position 113 is the position at which the reagent stirring rod 109 stirs a magnetic-particle reagent contained in the reagent vessel 116 that lies at that position. While the reagent vessel 116 containing a magnetic-particle reagent positioned at the inner-disk-111 side is stirred by the reagent stirring rod 109, the reagent(s) in one or a plurality of vessels 116-118 positioned at the outer-disk-110 side can be suctioned or dispensed by one or two of the reagent suctioning probes 108 depending on attributes to be analyzed. Basically, the reagent stirring rod 109 located at the dispensing/stirring position 113 stirs a reagent which is to be used in a next analysis cycle. In other words, during a cycle transition from one to the next, a reagent vessel transfer mechanism (not illustrated) moves a container 100 for which a magnetic-particle reagent stirring operation has been completed from the inner disk 111 to the outer disk 110. During the next cycle, then, the stirred magnetic-particle reagent is dispensed. It should be noted that in the case of an urgent analysis or depending on attributes to be analyzed, a reagent may also be dispensed from any one of reagent vessels 116 to 118 that lie at the inner-disk-side dispensing/stirring position 113. In this case, while the reagent vessel 116 containing a magnetic-particle reagent positioned at the inner-disk-111 side is stirred by the reagent stirring rod 109, the reagent(s) in one or two vessels 116-118 positioned at the inner-disk-111 side can be suctioned or dispensed by one or two of the reagent suctioning probes 108 depending on attributes to be analyzed. If the reagent vessel 116 containing a magnetic-particle reagent positioned at the inner-disk-111 side is not stirred by the reagent stirring rod 109, the reagent(s) in one or a plurality of vessels 116-118 positioned at the inner-disk-111 side can be suctioned or dispensed by one or two of the reagent suctioning probes 108 depending on attributes to be analyzed.

Regarding the accesses of the reagent suctioning probe 108 and reagent stirring rod 109, only the necessary reagent vessel is opened just before the access and closed just after the access by the device for opening/closing the lids of reagent vessels 121. Detailed operation of the device for opening/closing the lids of reagent vessels 121 will be explained hereinafter.

The outer circumference of the reagent disk 120 is covered with a reagent refrigerator 115 so that reagents contained in all the reagent vessel sets can be kept at a low temperature. Although not illustrated in FIGS. 1 and 2, a top cover is placed over the reagent disk 120 so that the reagent disk 120, including the device for opening/closing the lids of reagent vessels 121 and the refrigerator 115, can be completely covered. The top cover acts as a thermal insulation wall to enhance the cooling performance of the reagent disk 120 and also prevents dust or foreign particles from entering the reagent disk 120.

Figure 4:
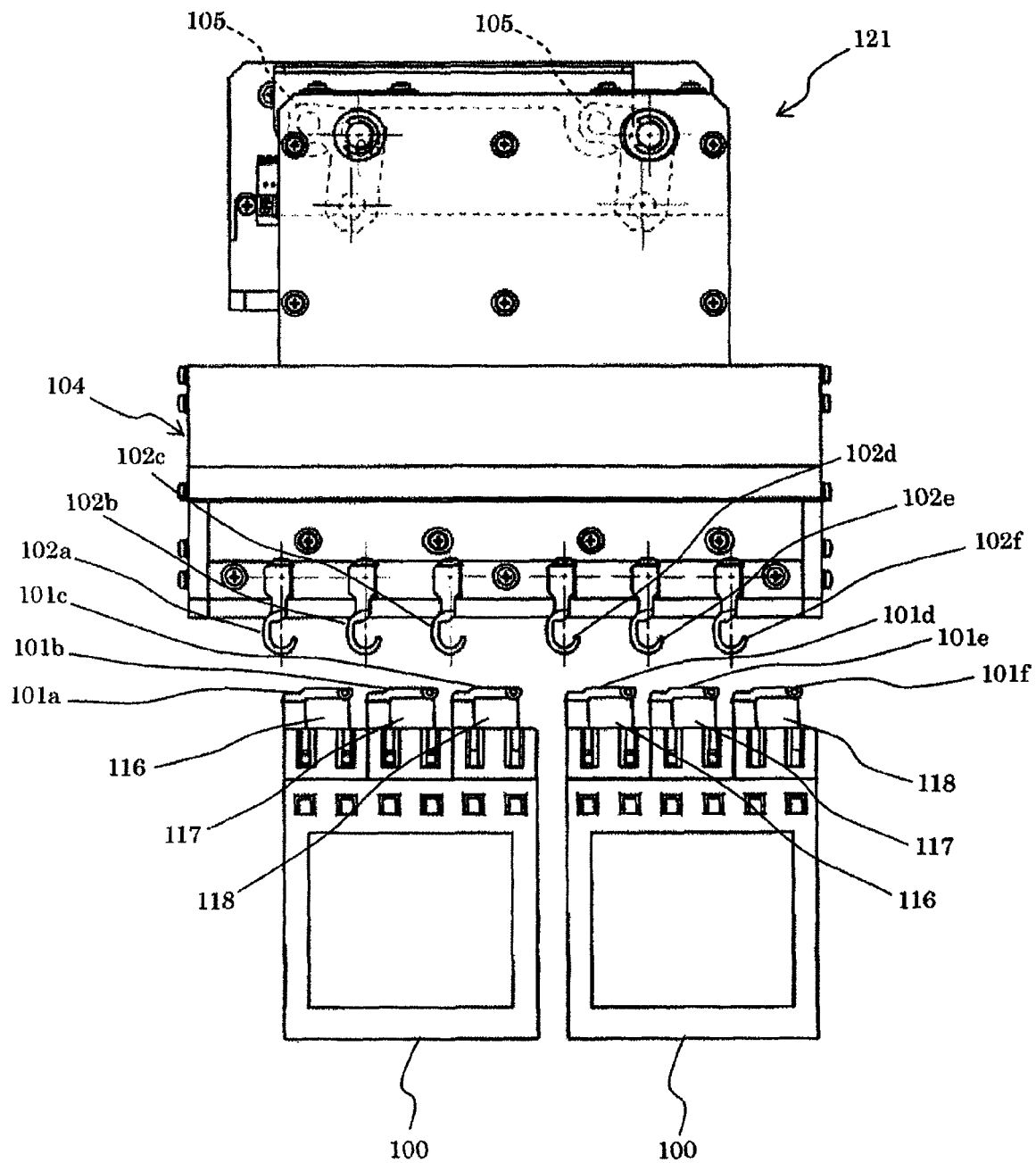
FIG. 4 is a front view of the device for opening/closing the lids of reagent vessels when its hook base is in a reference position.

FIG. 3 is a perspective view of the device for opening/closing the lids of reagent vessels 121, and FIG. 4 is its front view when viewed from a rotational direction of the reagent disk 120.

The device for opening/closing the lids of reagent vessels 121 includes the following components: a unit base 107 which is to be fixed to the frame 114; a hook base 104 connected to the unit base 107; a hook-base drive unit 106 that moves the hook base 104 with respect to the unit base 107 (i.e., in opening/closing directions of the lids 101 of sample vessels 116 to 118); and hooks 102 attached to the hook base 104. Although not illustrated in FIG. 3, the hook base 104 includes multiple hook drive mechanisms each adapted to slide one of the hooks 102 with respect to the hook base 104 and engage/disengage that hook 102 with/from the lid 101 of sample vessel.

As stated above, one set of reagent vessels 116 to 118 is contained in a container 100. Thus, one container 100 can store three types of reagent when its reagent vessels 116 to 118 contain mutually different reagents. Also, in the present embodiment, two sets of reagent vessels 116 to 118 are arranged at the dispensing/stirring position 113 which extends in a radial direction of the reagent disk 120. At the dispensing/stirring position 113, the two containers 100 that each contain a reagent vessel set are fixed so as not to move, but a certain degree of looseness is permissible.

While the present embodiment assumes that two sets of reagent vessels 116 to 118 are arranged at the dispensing/stirring position 113, the automated analyzer may instead be constructed so as to arrange only one reagent vessel set or three sets or more at the dispensing/stirring position 113, based on the size of the reagent disk 120. In addition, while one container 100 is assumed to have three reagent vessels 116 to 118, the container 100 can instead have two reagent vessels or four vessels or more. Further, reagent vessels 116 to 118 may not necessarily be divided into sets.

The unit base 107 is secured to the frame 114 by bolts or the like and does not move with respect to the reagent disk 120. The hook-base drive unit 106 is secured to the unit base 107 by brackets or the like. In the present embodiment, the hook-base drive unit 106 is a pulse motor although other types of motor or cylinders are also applicable.

The hook base 104 is connected to the hook-base drive unit 106 by a parallel link mechanism comprising two arms 105. The hook-base drive unit 106 drives the arms 105 so that the hook base 104 moves in opening/closing directions of the lids 101 of reagent vessels 116 to 118 (see FIG. 7 in which the dotted arrows represent opening directions of the lids 101 and the solid arrow represents the movement of the hook base 104). In the present embodiment, all the lids 101 exhibit arc motions when they open or close. Thus, the hook base 104, too, exhibits an arc motion when it moves.

The hooks 102 are adapted to hook the lids 101 of reagent vessels 116 to 118. The hooks 102 are attached to a lower section of the hook base 104 so as to be aligned in a radial direction of the reagent disk 120. In the present embodiment, the number of the hooks 102 is six, which is the same as the number of reagent vessels (116 to 118) aligned at the dispensing/stirring position 113. Of course, the number of the hooks 102 can be adjusted based on the number of reagent vessels (116 to 118) to be aligned at the dispensing/stirring position 113. The hooks 102 are each connected via a hook shaft 103 to the output shaft of a hook drive mechanism (not illustrated) inside the hook base 104. Each of the hook drive mechanisms moves one of the hooks 102 around its hook shaft 103 so as to change the posture of that hook 102 between the engagement position at which the hook 102 hangs downward and the disengagement position at which the hook 102 is tilted toward a horizontal direction. In the present embodiment, each of the hook drive mechanisms is a pulse motor although other types of motor or cylinders are also applicable.

The engagement position specifically refers to the position at which a hook 102 hangs downward so as to hook the lid 101 of a reagent vessel (116, 117, or 118). The disengagement position, on the other hand, refers to the position at which a hook 102 is tilted toward a horizontal direction so as to be disengaged from the lid 101 of a reagent vessel (116, 117, or 118).

Discussed next is the operation of the above-described reagent vessel opening/closing device 121.

The device for opening/closing the lids of reagent vessels 121 selectively engages the hooks 102 with particular lids 101 of two reagent vessel sets (i.e., six reagent vessels 116 to 118). After the engagement, the device for opening/closing the lids of reagent vessels 121 moves the hook base 104 in an opening or closing direction so as to open or close the particular lids 101. Assume, for example, that the device for opening/closing the lids of reagent vessels 121 is to open the lid 101 of a reagent vessel 117 located on the inner-disk-111 side of the dispensing/stirring position 113. In that case, the device for opening/closing the lids of reagent vessels 121 first lowers the hook base 104 to a lower position and then places the associated hook 102 in its engagement position to engage that hook 102 with the lid 101 of the reagent vessel 117. Thereafter, the device for opening/closing the lids of reagent vessels 121 drives the hook-base drive unit 106 to move the hook base 104 to an upper position, thereby lifting the lid 101 which has been engaged with the hook 102. When closing the lifted lid 101 of the reagent vessel 117, on the other hand, the device for opening/closing the lids of reagent vessels 121 drives the hook-base drive unit 106 to move the hook base 104 from the upper position to the lower position, with the associated hook 102 placed in its engagement position. By doing so, the hook 102 presses the lid 101 of the reagent vessel 117 downward. In other words, when the lid 101 of the reagent vessel 117 is closed after being opened, the hook base 104 just needs to be lowered to the lower position after the opening, without changing the posture of the hook 102.

The above lid opening/closing sequence is described more in detail with reference to FIGS. 4 to 8. In those figures, the bold solid arrows represent the movement of the hook base 104, the non-bold solid arrows represent the movement of the hooks 102, and the dotted arrows represent the motion of the lids 101 of reagent vessels 116 to 118. Note that in those figures, the hooks 102 and the lids 101 are followed by the letters 'a' to 'f' from left to right (e.g., the hooks 102a, 102b, 102c, . . . ; the lids 101a, 101b, 101c, . . . ).

FIG. 4 illustrates the hook base 104 when it is in an upper position (also referred to as the reference position). As illustrated, the lids 101a to 101f of reagent vessels 116 to 118 are all closed, and the hook base 104 stays at the upper position. The hooks 102a to 102f all hang downward.

Figure 5:
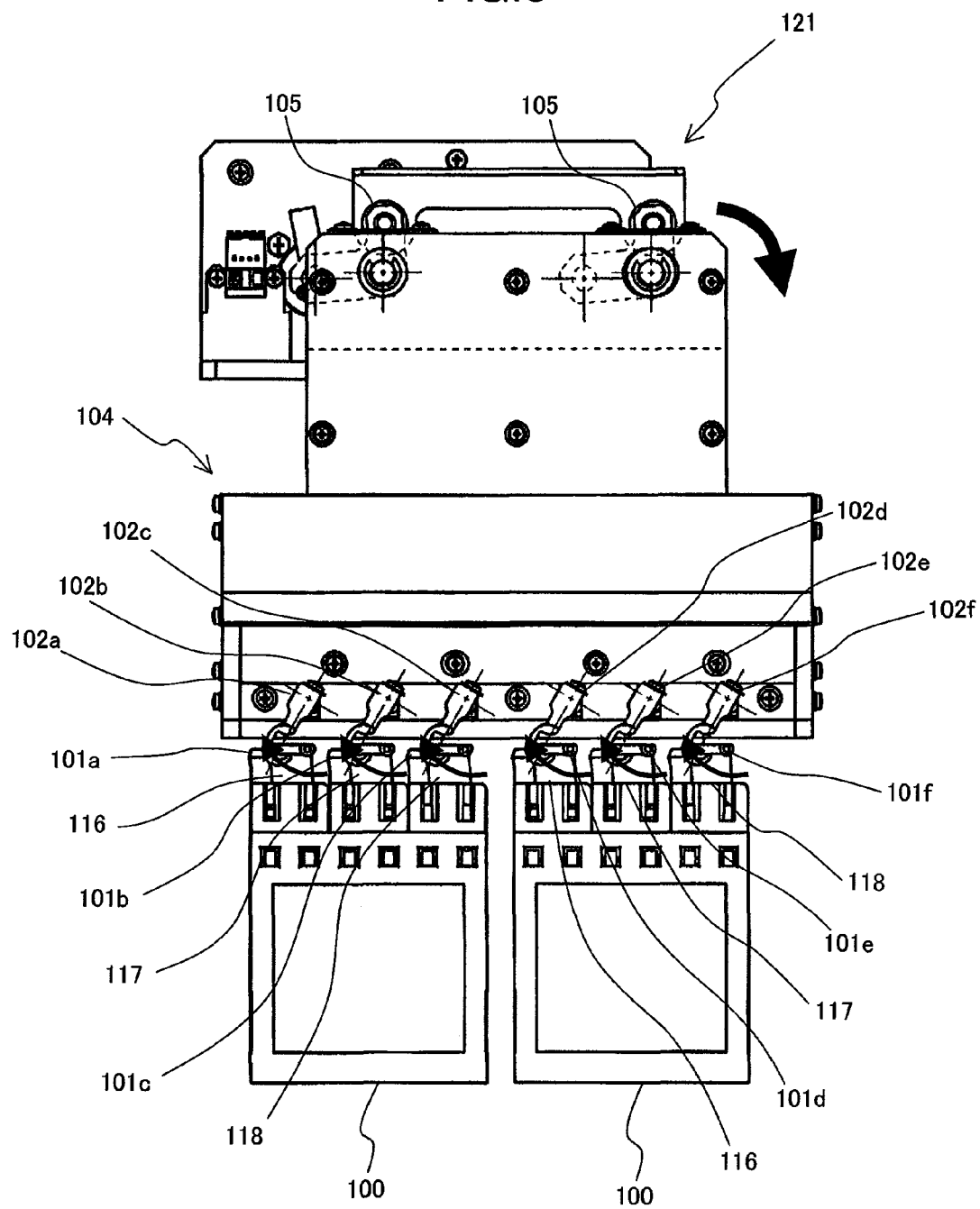
FIG. 5 is a front view of the device for opening/closing the lids of reagent vessels when its hooks are about to hook the lids of reagent vessels.

FIG. 5 illustrates the hooks 102a to 102f when they are about to hook the lids 101a to 101f of the reagent vessels 116 to 118. The hook base 104 has been moved by the arms 105 from the upper position shown in FIG. 4 to a lower position. The hooks 102a to 102f are tilted clockwise by a given angle so as not to touch the lids 101a to 101f.

Figure 6:
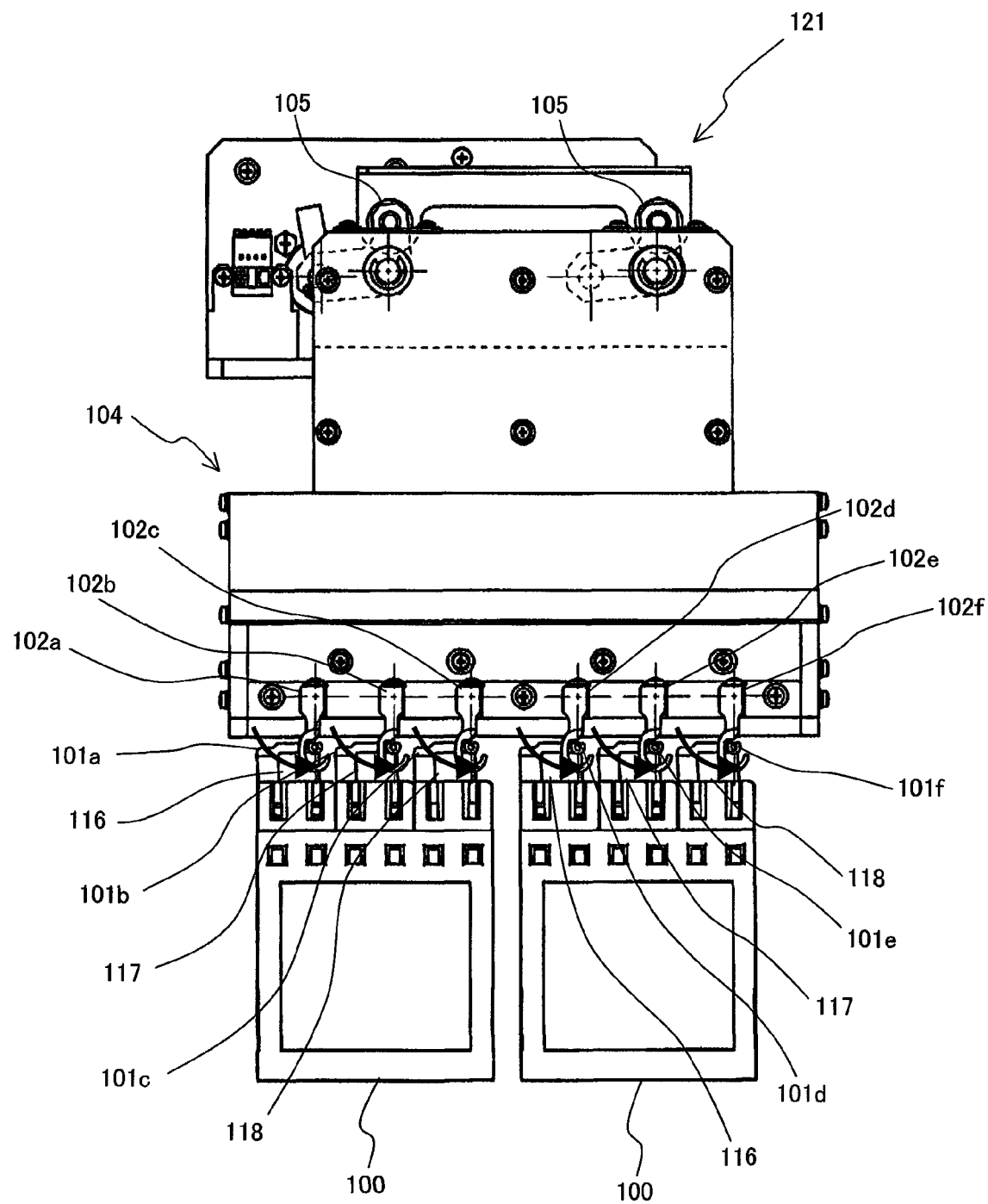
FIG. 6 is a front view of the device for opening/closing the lids of reagent vessels when the hooks are hooking the lids of reagent vessels.

FIG. 6 illustrates the hooks 102a to 102f when they are hooking the lids 101a to 101f of the reagent vessels 116 to 118. The hooks 102a to 102f are now in their respective engagement positions to hook the lids 101a to 101f of the reagent vessels 116 to 118.

Figure 7:
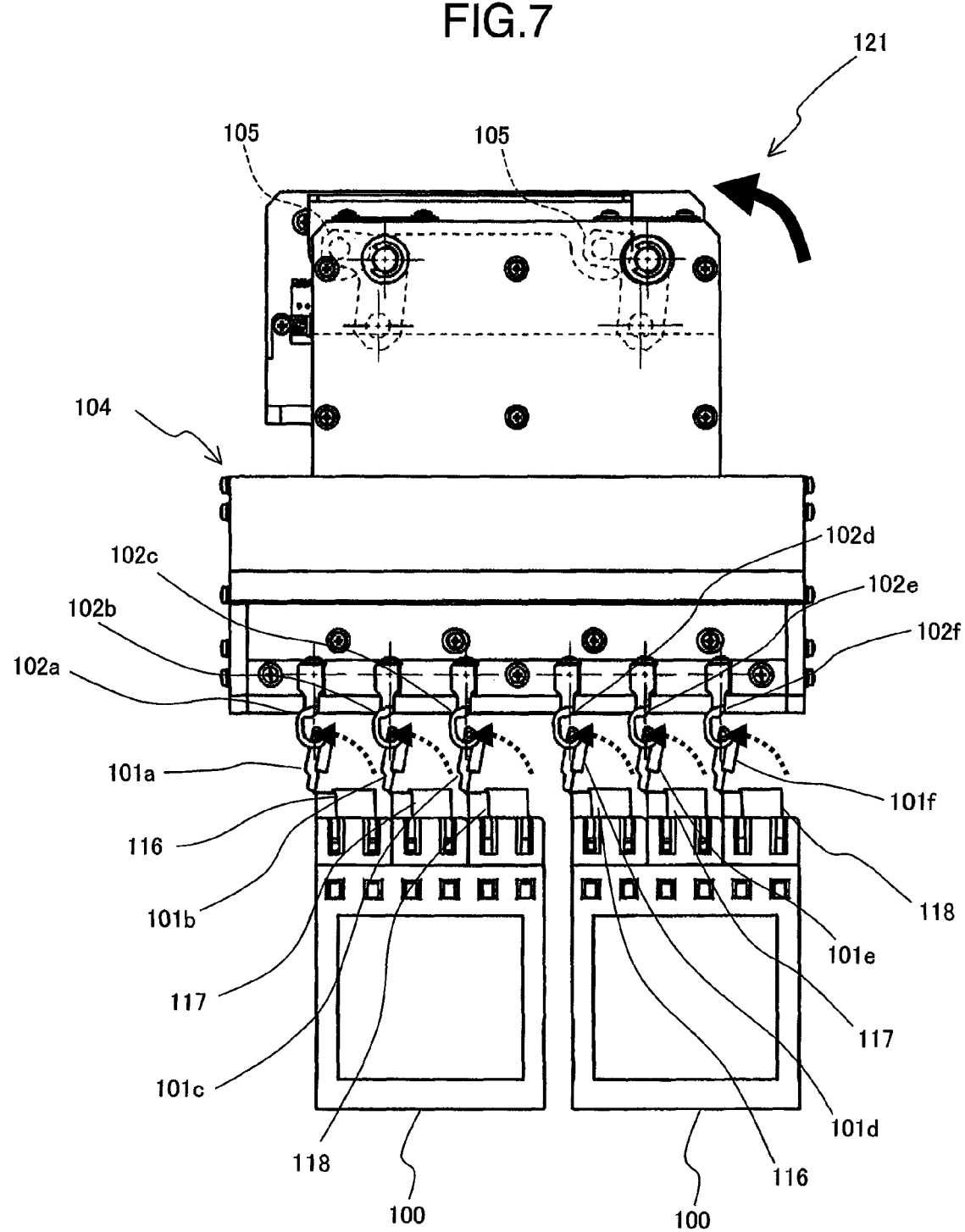
FIG. 7 is a front view of the device for opening/closing the lids of reagent vessels when the hooks are lifting the lids of reagent vessels.

FIG. 7 illustrates the lids 101a to 101f of the reagent vessels 116 to 118 when they are lifted (i.e., opened). Moved by the hook-base drive unit 106 in an opening direction, the hook base 104 is now in the upper position again.

Figure 8:
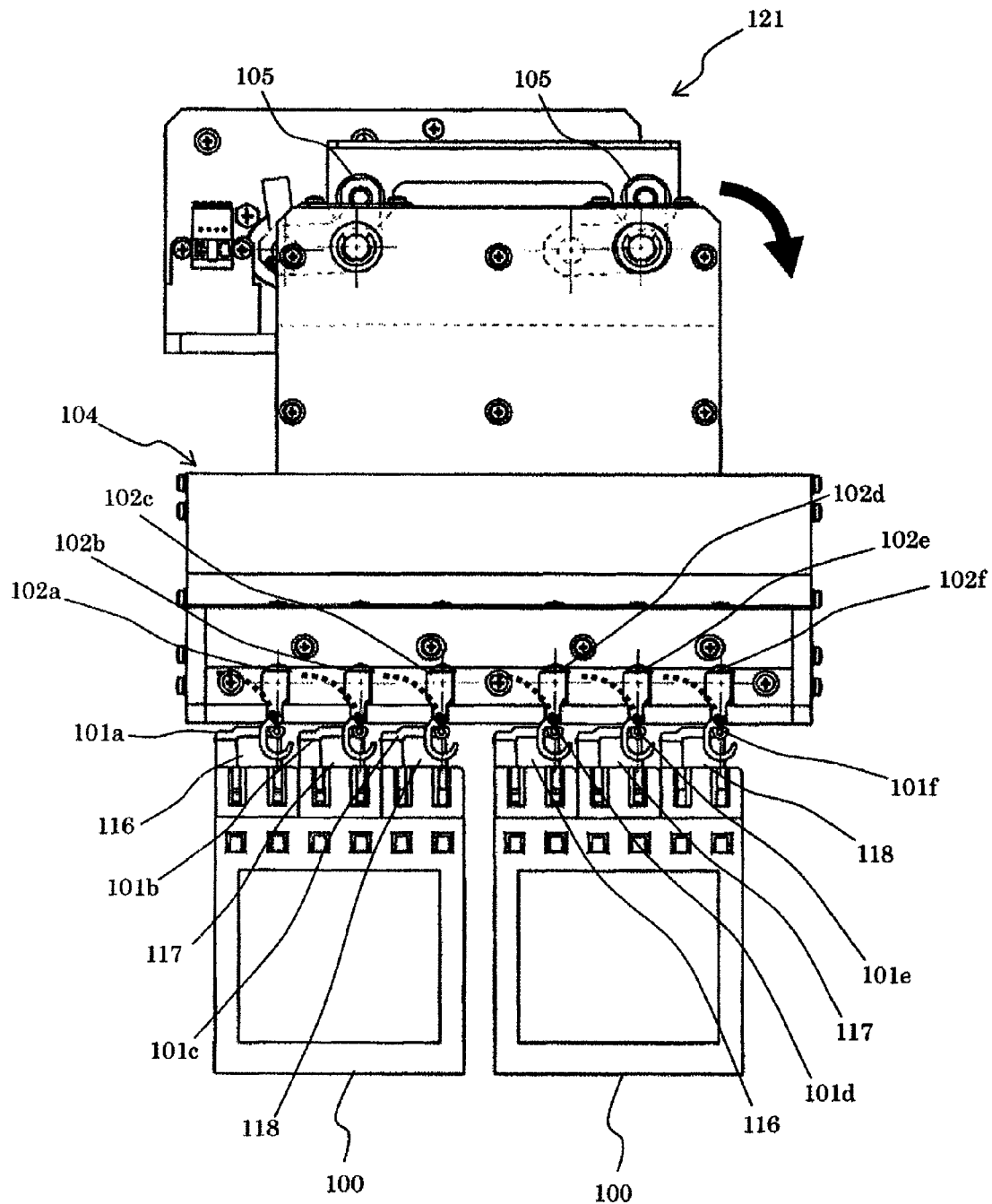
FIG. 8 is a front view of the device for opening/closing the lids of reagent vessels when the hooks are pressing the lids of reagent vessels downward.

FIG. 8 illustrates the lids 101a to 101f of the reagent vessels 116 to 118 when they are closed after the state of FIG. 7. Moved by the hook-base drive unit 106 in a closing direction, the hook base 104 is now in a lower position which is slightly lower than the lower position of FIG. 6. Placing the hook base 104 in the further lower position allows the proximal portions of the hooks 102a to 102f to press the lids 101a to 101f downward, thereby reliably closing the lids 101a to 101f.

To place the device for opening/closing the lids of reagent vessels 121 of FIG. 8 back in the state of FIG. 4, the hooks 102a to 102f are first placed in their respective disengagement positions as in FIG. 5, and the hook base 104 is then moved in an opening direction to be placed in the upper position of FIG. 4. Thereafter, the hooks 102a to 102f are placed in their respective engagement positions so that the hooks 102a to 102f hang downward.

FIGS. 4 to 8 are merely an example in which the lids 101a to 101f of six reagent vessels 116 to 118 are opened or closed simultaneously. The device for opening/closing the lids of reagent vessels 121 of the present embodiment is also capable of selectively opening or closing the lids 101a to 101f by individually controlling the hooks 102a to 102f during the movement of the hook base 104. Assume, for example, that the device for opening/closing the lids of reagent vessels 121 opens or closes a reagent vessel 117 in a container 100 located on the inner disk 111 (the left containers 100 of FIGS. 4 to 11 are the ones located on the inner disk 111). During the transition from the state of FIG. 5 to the state of FIG. 6, only the hook 102b is placed in its engagement position with the rest of the hooks (102a, 102c, . . . , 102f) placed in their respective disengagement positions. During the operation of FIG. 7, then, the hook 102b opens the lid 101b only. To close the lid 101b, the operation of FIG. 8 just needs to be performed. With the operation of FIG. 8, the hook 102b, now in its engagement position, closes the lid 101b whereas the rest of the hooks (102a, 102c, . . . , 102f), now in their respective disengagement positions, do not touch the rest of the lids (101a, 101c, . . . , 101f).

After particular reagent vessels are opened, the reagent suctioning probes 108 or the reagent stirring rod 109 accesses the opened reagent vessels. For example, when a reagent vessel 116 contains a solution including a magnetic-particle reagent, which tends to precipitate, the reagent stirring rod 109 needs to stir the solution so that the reagent can be uniformly distributed in the solution. This stirring takes a relatively long time, and the reagent stirring rod 109 has to be within the reagent vessel 116 for a longer amount of time than the reagent suctioning probes 108 have to be within other reagent vessels. When, for example, the reagent stirring rod 109 and one of the reagent suctioning probes 108 simultaneously access a reagent vessel 116 and reagent vessel 117, respectively, which vessels require different access times due to different solutions contained, the suctioning operation may be completed before the stirring operation. Therefore, for the purpose of preventing reagent evaporation or deterioration, it is necessary to close the lid 101b of the reagent vessel 117 as soon as possible after the completion of the suctioning operation, even if the stirring operation has not been completed for the reagent vessel 116. The possibility to perform a stirring operation in one (or more) reagent vessel(s) and a suctioning operation in one (or more) other reagent vessel(s) in a parallel, but independent manner allows also an optimization of the workflow and can lead to an increased test flow capacity, because different time-limiting steps (e.g. stirring, suctioning) which have to be performed in different reagent vessels can be performed in parallel and independent of each other.

The device for opening/closing the lids of reagent vessels 121 of the present embodiment is also effective in the above case.

Figure 9:
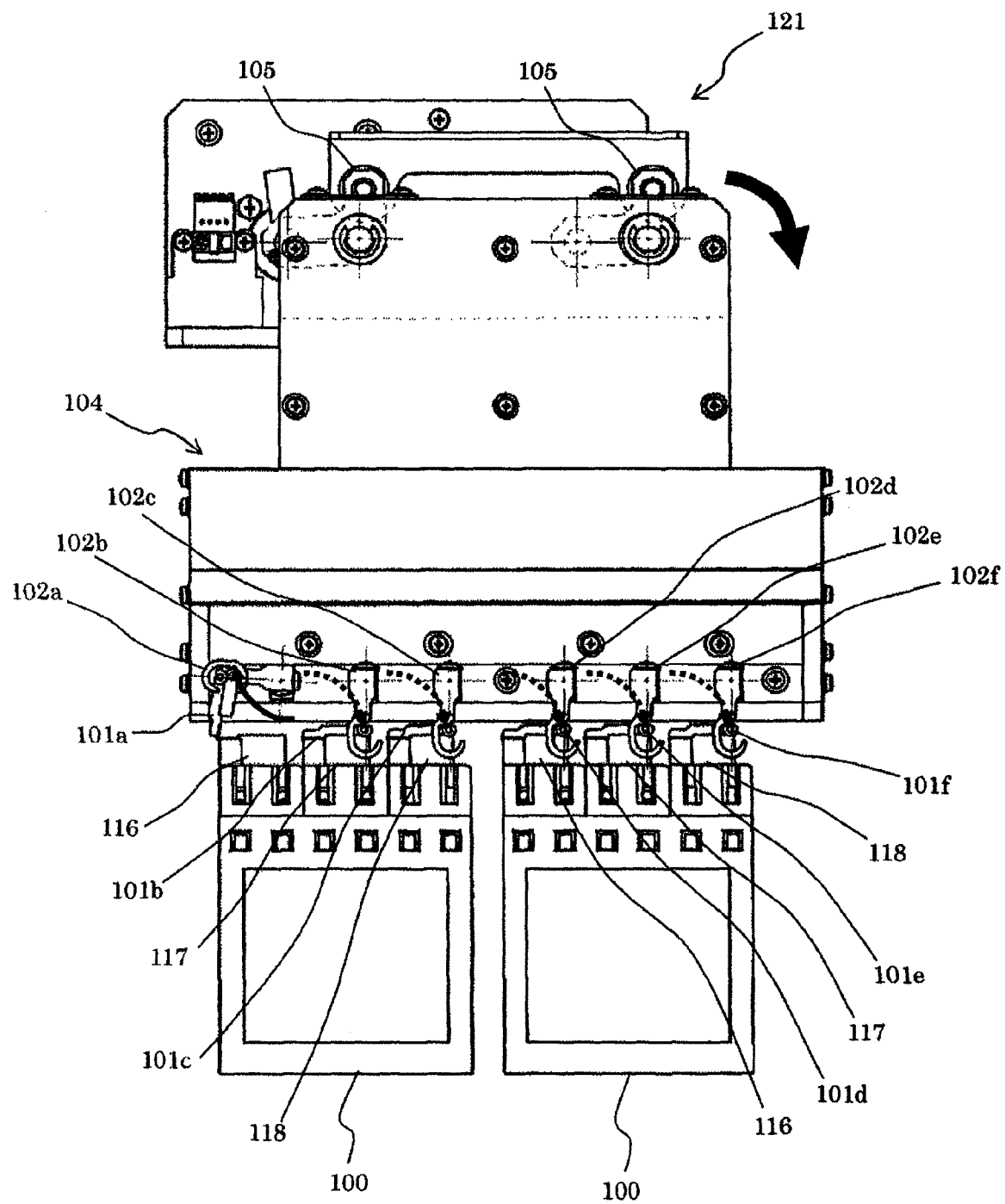
FIG. 9 is a front view of the device for opening/closing the lids of reagent vessels when one reagent vessel is kept open with the rest closed.

For example, as illustrated in FIG. 9, when the lids 101b to 101f are closed without closing the lid 101a, the hook-base drive unit 106 first moves the hook base 104 in a closing direction (i.e., toward a lower position), with the hooks 102b to 102f in their respective engagement positions. At the same time, the hook 102a is placed in its disengagement position with the lid 101a engaged with. This allows the lids 101b to 101f to be closed with the lid 101a kept open. That is to say, while the magnetic-particle reagent in the reagent vessel 116 is stirred by the reagent stirring rod 109 with the lid 101a of the vessel 116 kept open, the lids of other reagent vessels for which the suctioning/dispensing operation had been finished can be closed. In this case, the hook 102a moves to its nearly horizontal posture in order to keep open the lid 101a.

Figure 10:
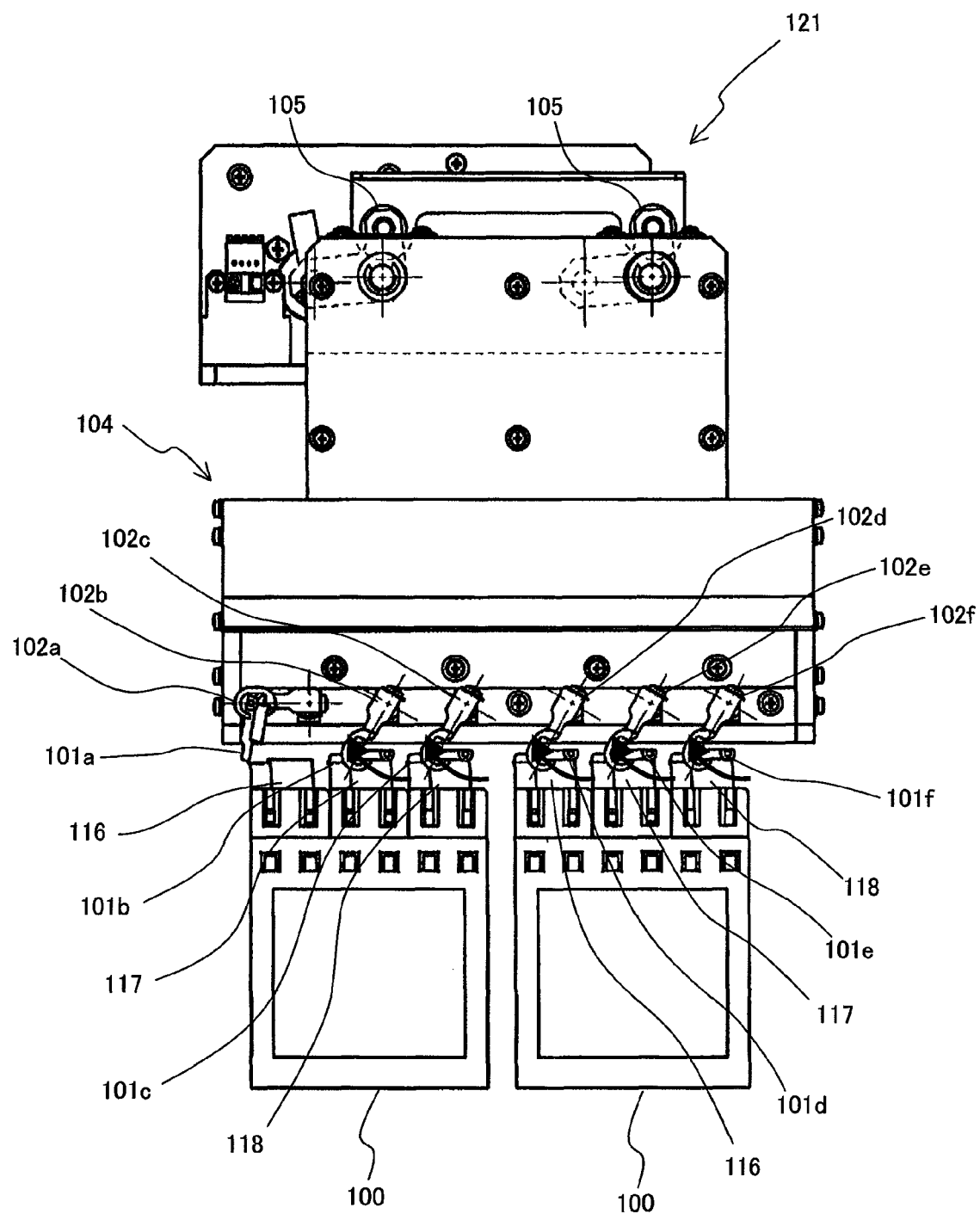
FIG. 10 is a front view of the device for opening/closing the lids of reagent vessels when one reagent vessel is kept open with the lids of the rest disengaged from their associated hooks.
Figure 11:
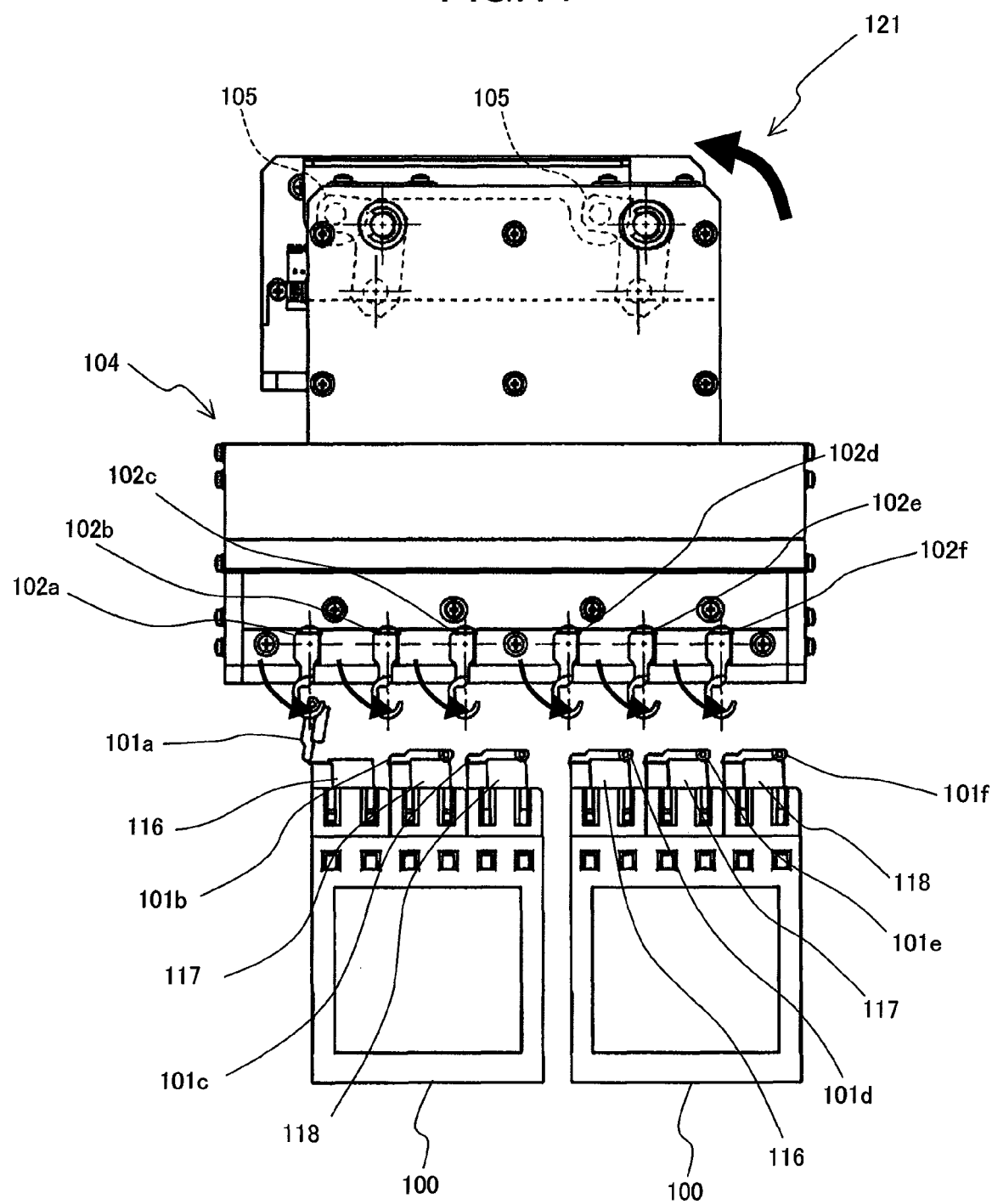
FIG. 11 is a front view of the device for opening/closing the lids of reagent vessel when the hook base is in the reference position again with one reagent vessel kept open.
Figure 12:
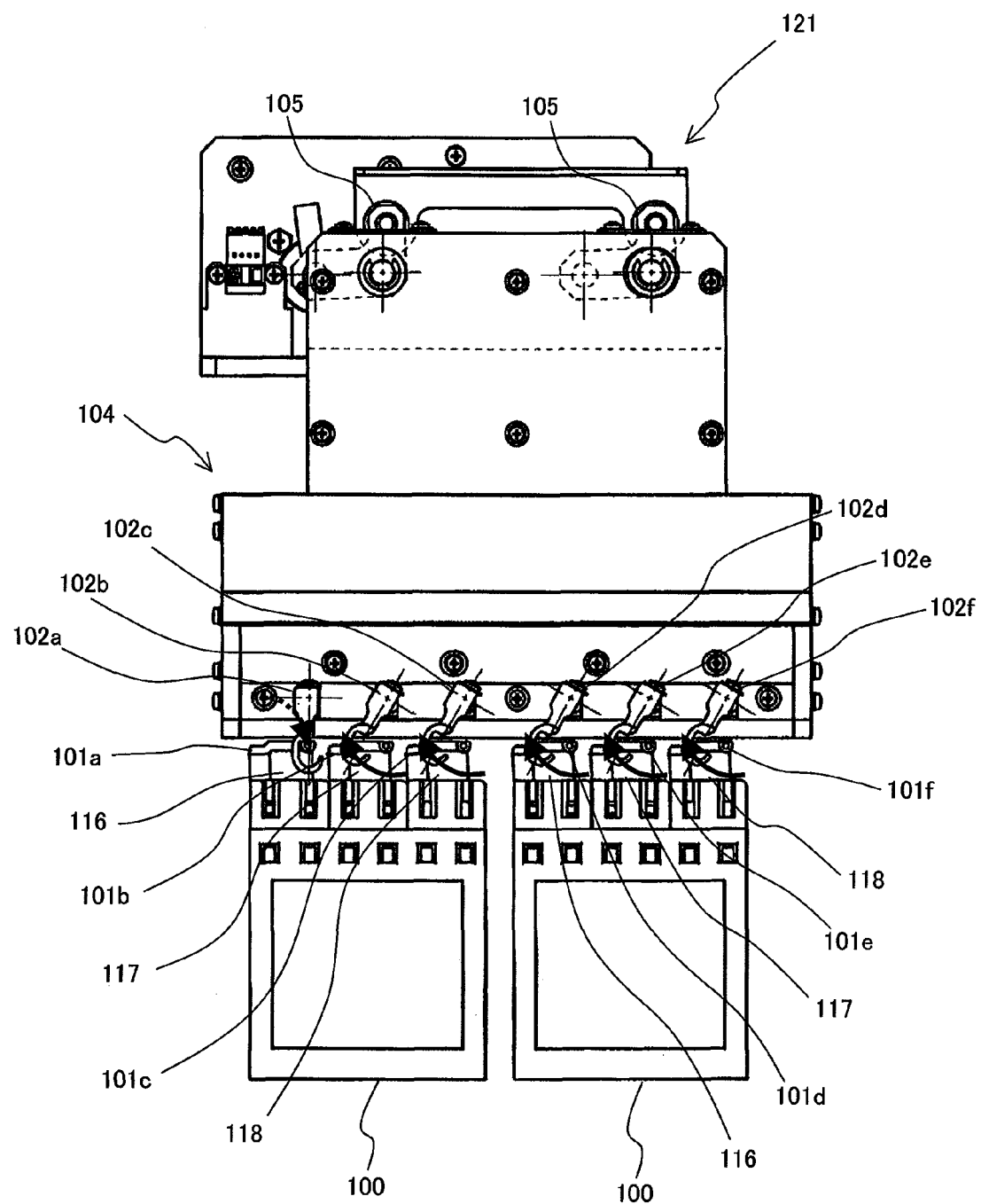
FIG. 12 is a front view of the device for opening/closing the lids of reagent vessels when only a particular reagent vessel is closed.

As illustrated in FIG. 10, when the open lid 101a is closed thereafter, the hook base 104 is first elevated slightly, and the hooks 102b to 102f engaged with the lids 101b to 101f are then moved to their respective disengagement positions so that the hooks 102b to 102f can be disengaged from the lids 101b to 101f. Next, as illustrated in FIG. 11, the hook base 104 is elevated to an upper position, and the hooks 102a to 102f are placed in their respective engagement positions. This results in the hook 102a hooking the lid 101a, with the hook base 104 placed at the reference position of FIG. 4. Finally, as illustrated in FIG. 12, the hook base 104 is moved toward a lower position, and at the same time, the hooks 102b to 102f are placed at their respective disengagement positions. This allows the hook 102a to press the lid 101a downward and close it. To place the hook base 104 back in the reference position (the state of FIG. 4) thereafter, the hook 102a needs to be disengaged from the lid 101a as in FIG. 5, and the hook base 104 is then elevated to the reference position.

Described next is the operation of the device for opening/closing the lids of reagent 121 during an analysis performed by the automated analyzer of the present embodiment.

Although not illustrated, the automated analyzer includes a control device. This control device is designed to control the hook-base drive unit 106 and hook drive mechanisms (not illustrated) of the device for opening/closing the lids of sample vessels 121 based on analysis request information, so that particular lids 101 can be opened during dispensing and stirring operations and can be closed upon the completion of those operations.

Figure 13:
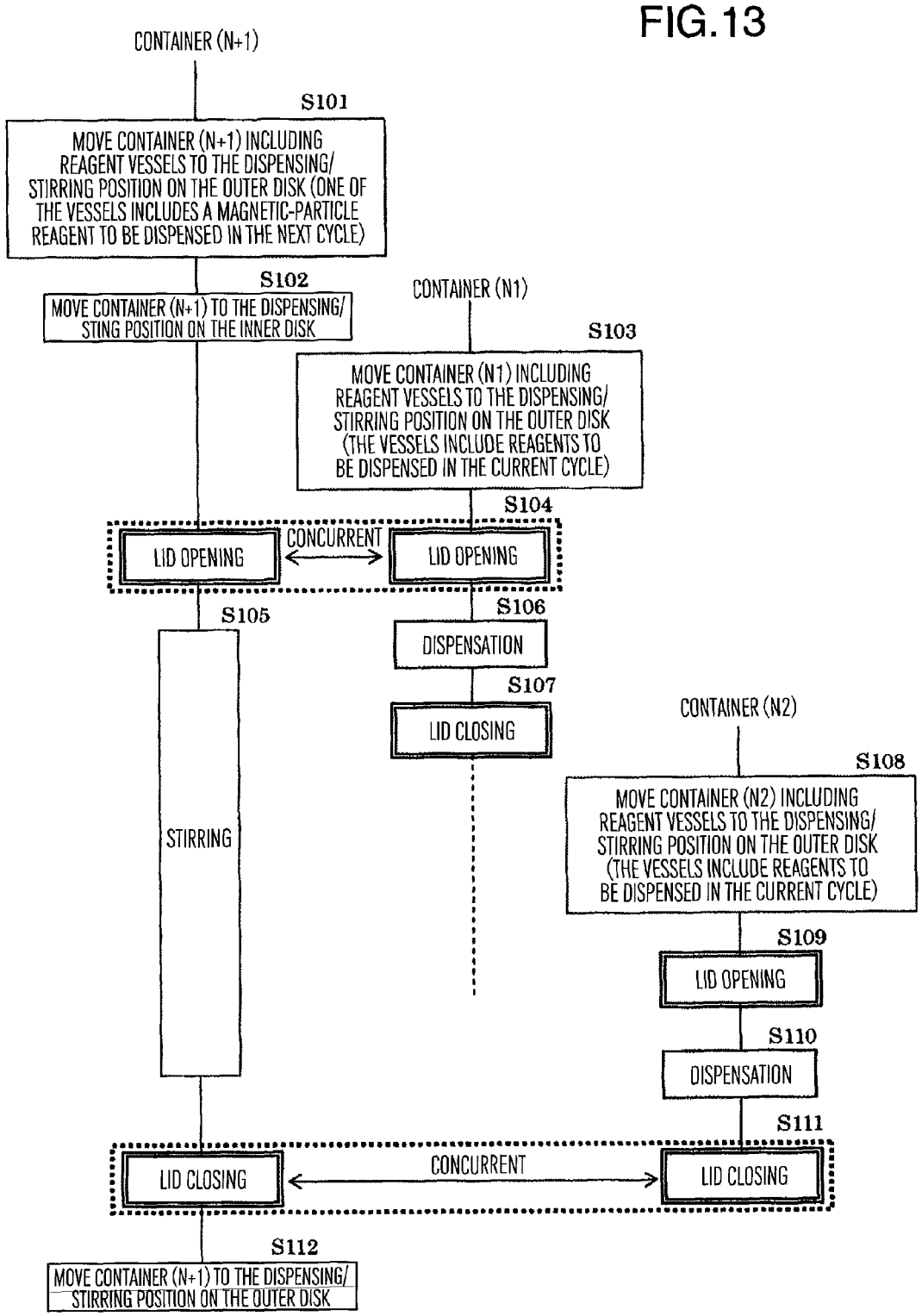
FIG. 13 is a flowchart illustrating the operation of a control device of the automated analyzer to control the device for opening/closing the lids of reagent vessels during an analysis.
Figure 14:
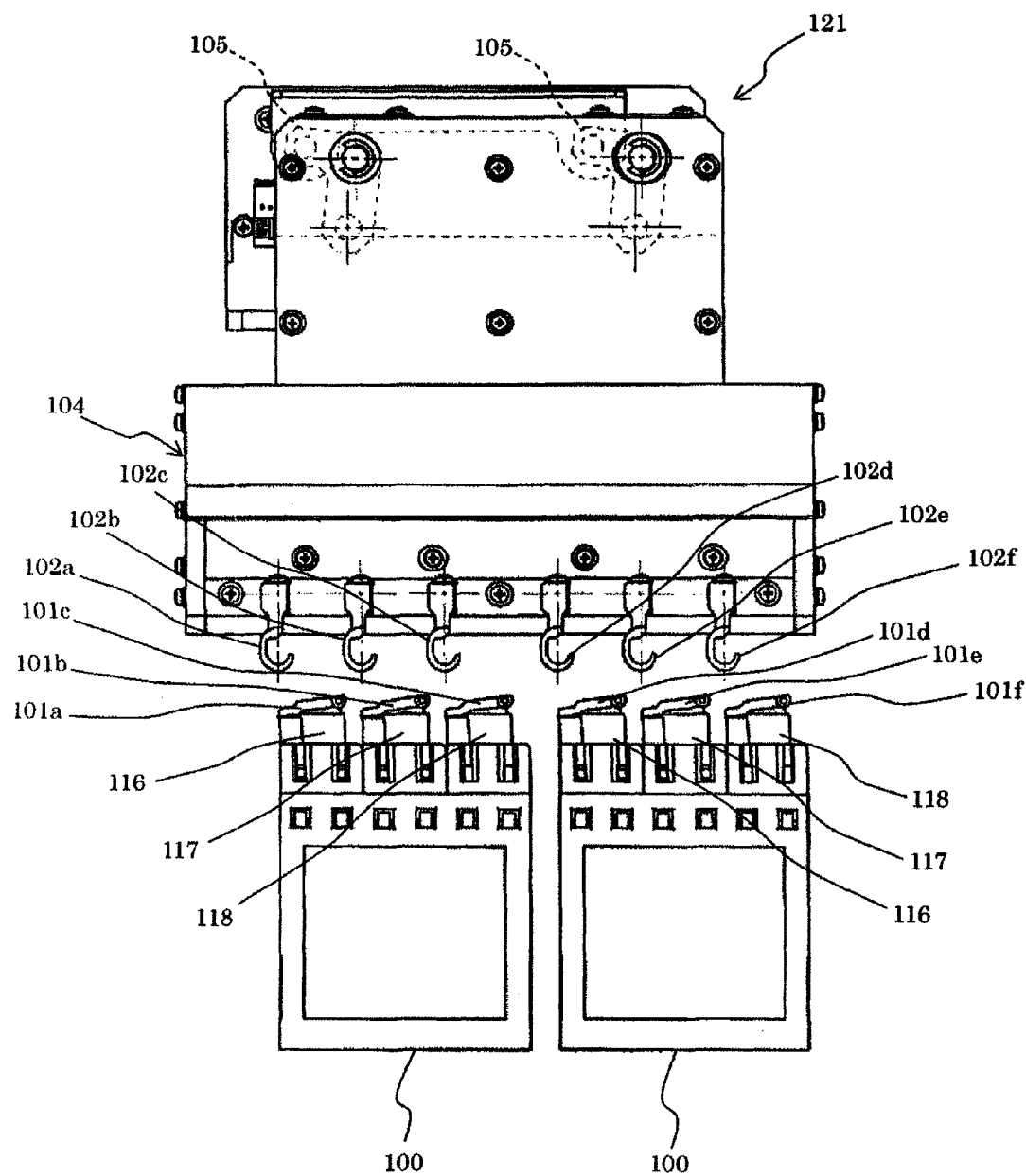
FIG. 14 is a diagram to illustrate partial vessel-lid closure and corresponds to FIG. 4.
Figure 15:
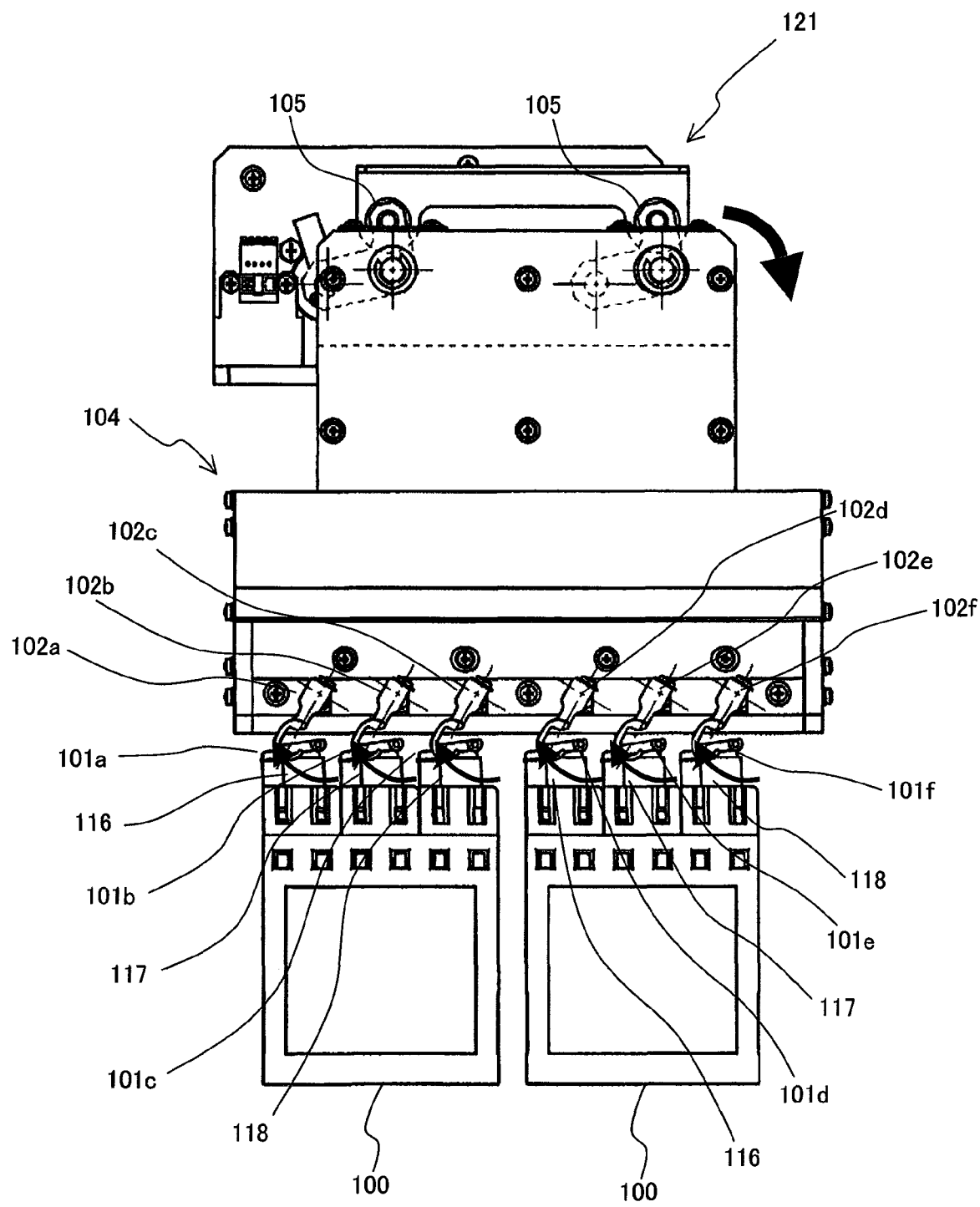
FIG. 15 is a diagram to illustrate partial vessel-lid closure and corresponds to FIG. 5.
Figure 16:
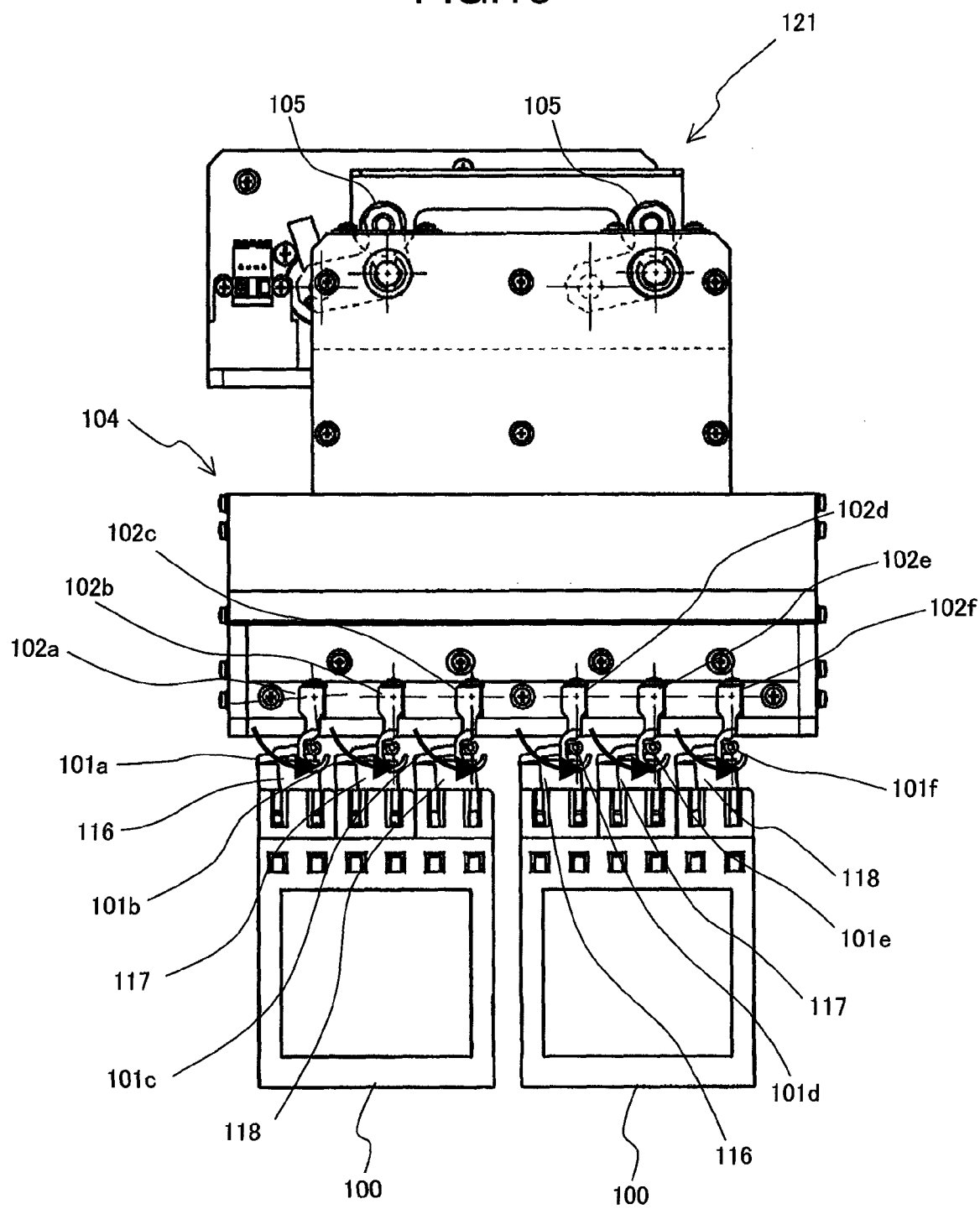
FIG. 16 is a diagram to illustrate partial vessel-lid closure and corresponds to FIG. 6.
Figure 17:
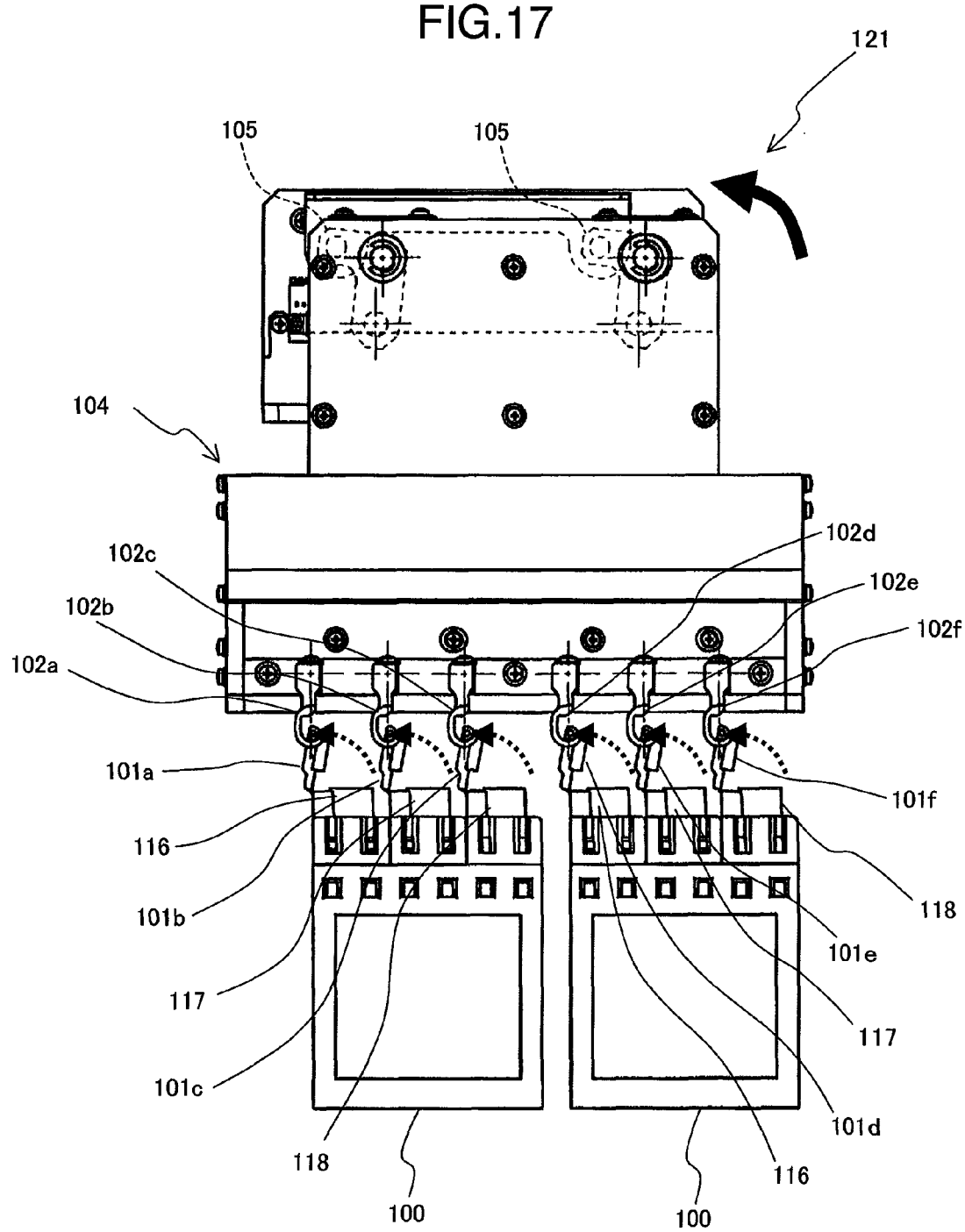
FIG. 17 is a diagram to illustrate partial vessel-lid closure and corresponds to FIG. 7.
Figure 18:
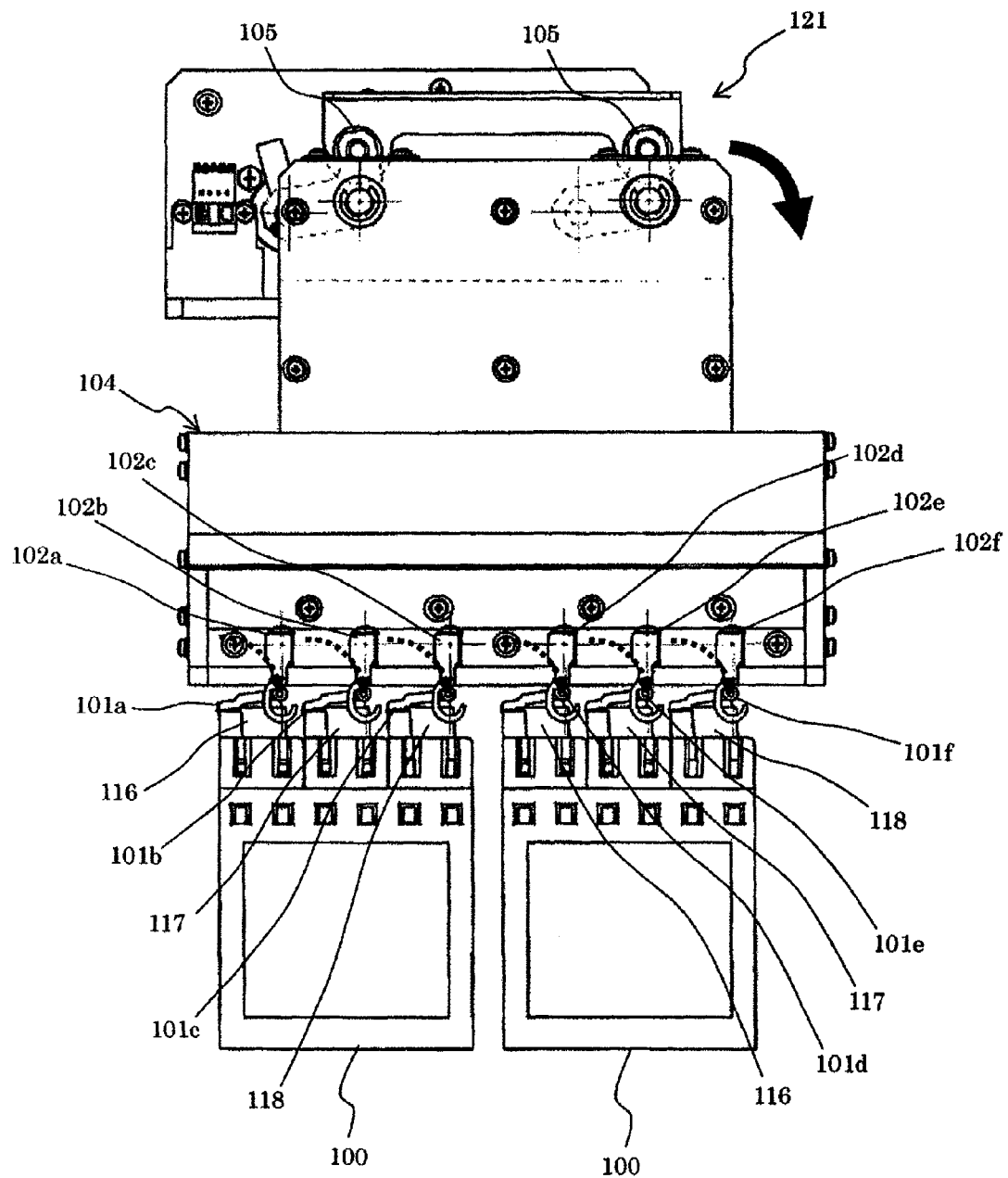
FIG. 18 is a diagram to illustrate partial vessel-lid closure and corresponds to FIG. 8.
Figure 19:
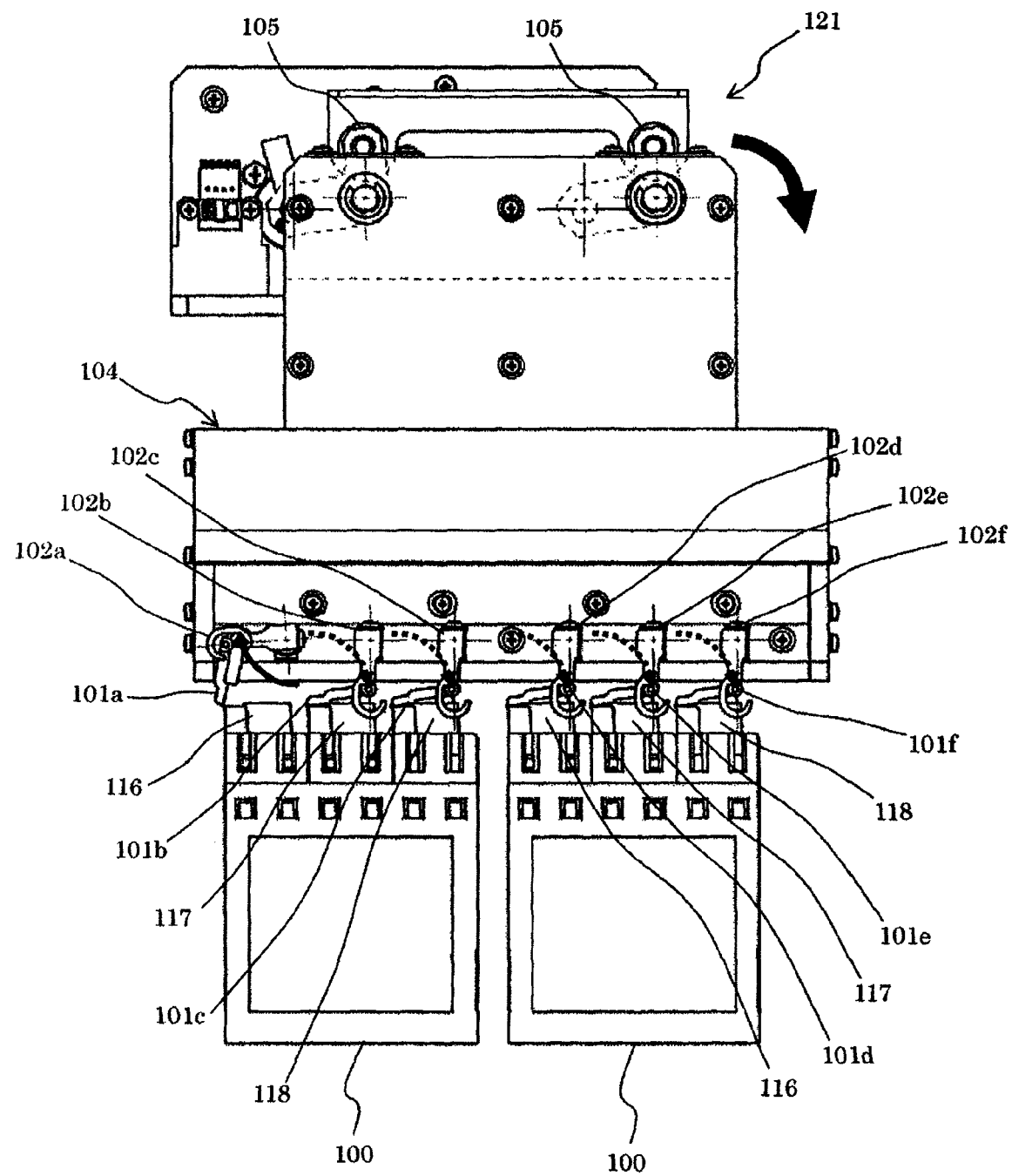
FIG. 19 is a diagram to illustrate partial vessel-lid closure and corresponds to FIG. 9.
Figure 20:
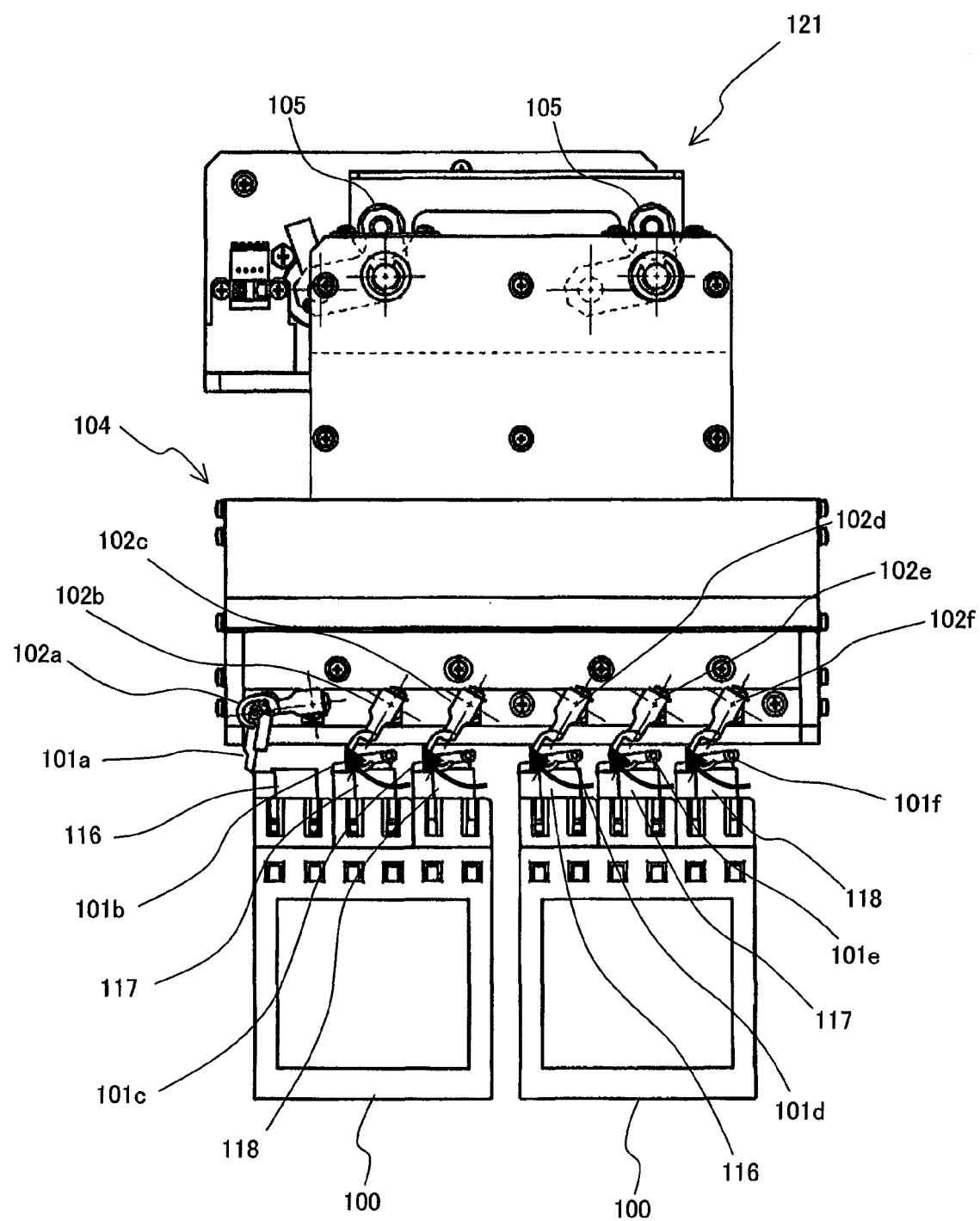
FIG. 20 is a diagram to illustrate partial vessel-lid closure and corresponds to FIG. 10.
Figure 21:
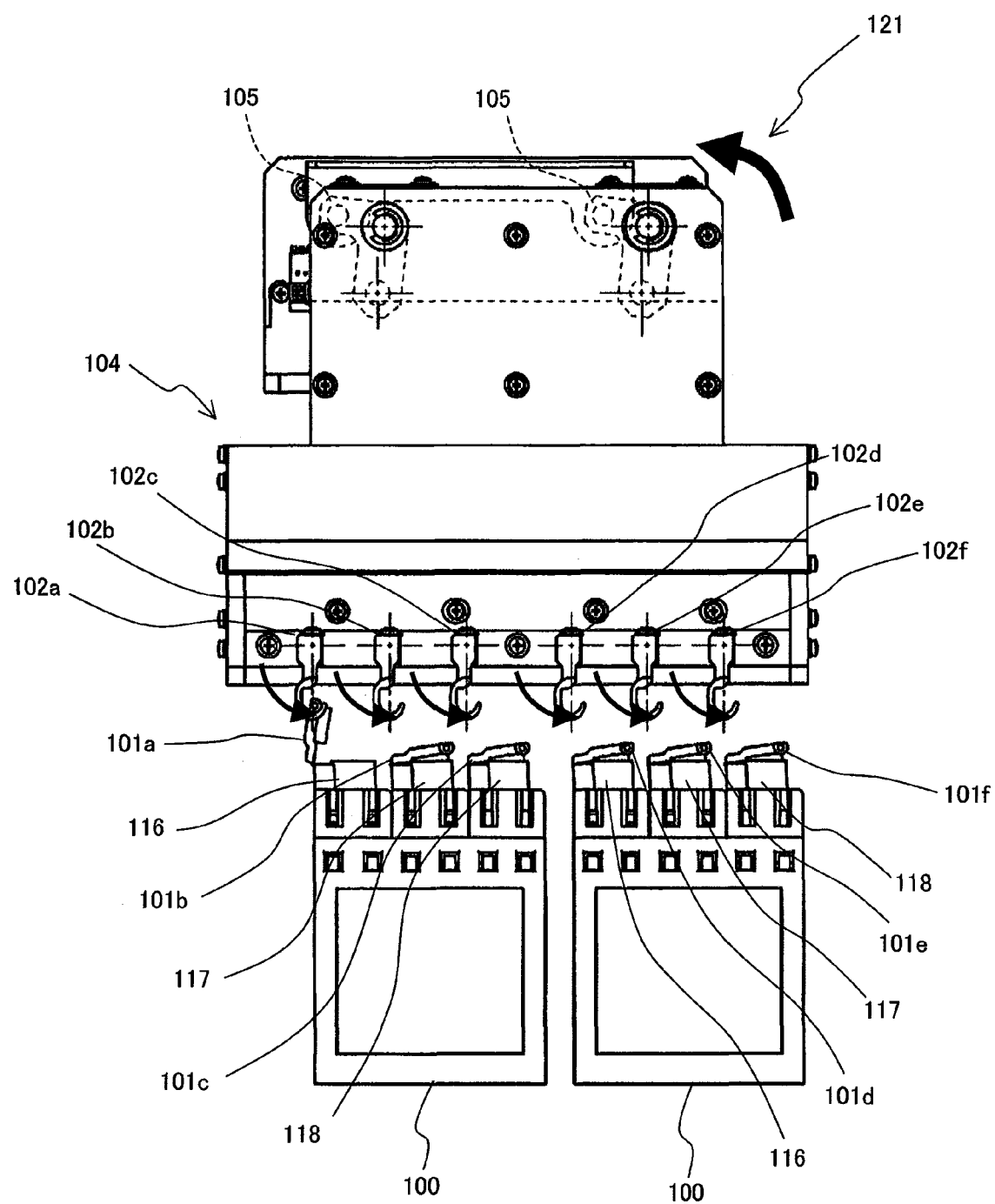
FIG. 21 is a diagram to illustrate partial vessel-lid closure and corresponds to FIG. 11.
Figure 22:
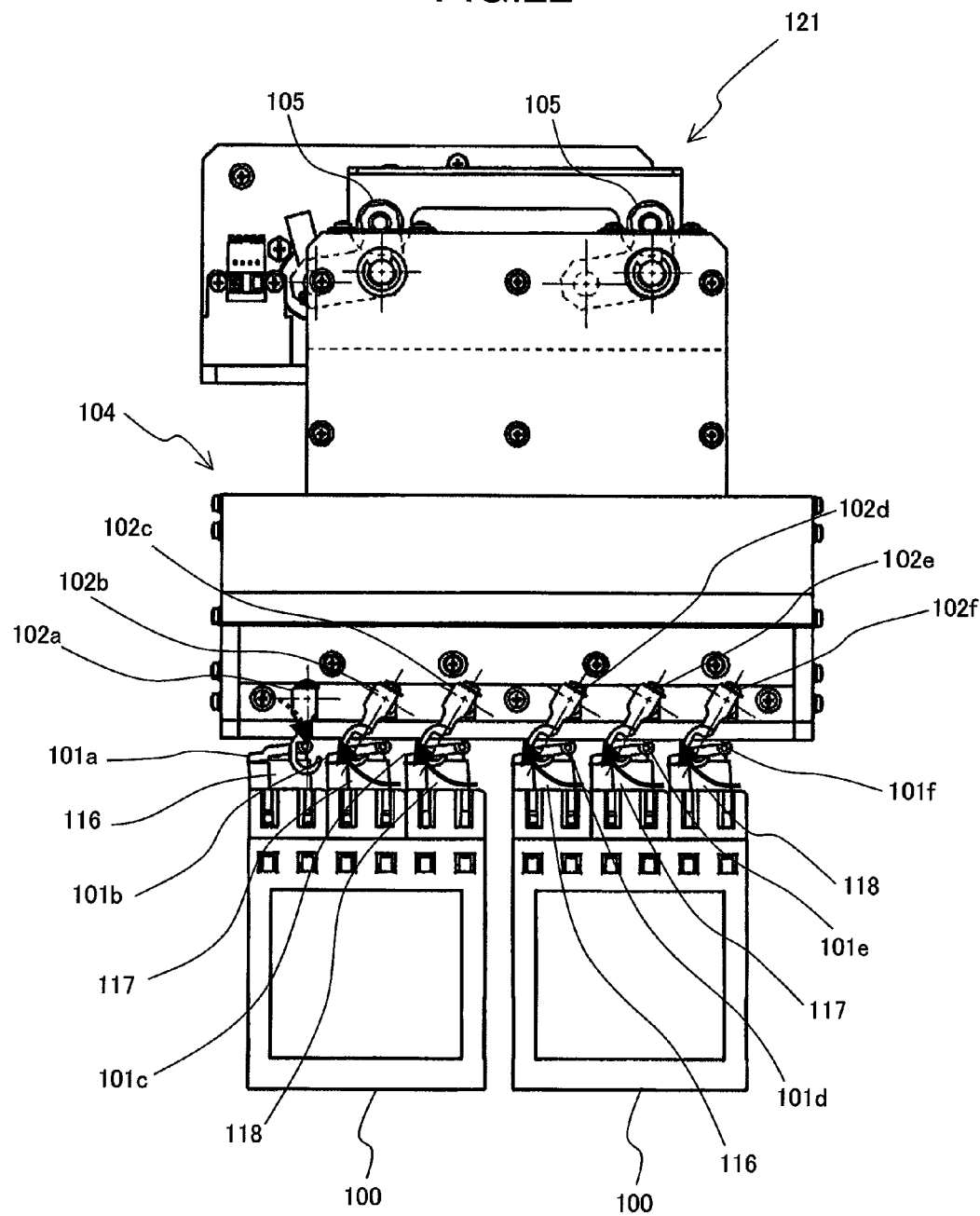
FIG. 22 is a diagram to illustrate partial vessel-lid closure and corresponds to FIG. 12.

FIG. 13 is a flowchart illustrating the operation of the control device to control the device for opening/closing the lids of reagent 121 during an analysis performed by the automated analyzer. In FIG. 13, the single-line boxes represent operations to be performed by the reagent disk 120, the reagent suctioning probes 108, and the reagent stirring rod 109 whereas the double-line boxes represent operations to be performed by the device for opening/closing the lids of reagent 121.

<Step S101>

The outer disk 110 is first rotated to move a container 100 that includes reagent vessels 116 to 118 to the dispensing/stirring position 113 located on the outer disk 110. The reagent vessel 116 contains a magnetic-particle reagent to be dispensed one cycle later. At this point, no container 100 is placed at the dispensing/stirring position 113 located on the inner disk 111. In the explanation that follows with regard to FIG. 13, the above container 100 is instead referred to as the container (N+1).

<Step S102>

A reagent transfer mechanism (not illustrated) transfers the container (N+1), which is located at the dispensing/stirring position 113 on the outer disk 110, to the dispensing/stirring position 113 located on the inner disk 111.

<Step S103>

The outer disk 110 is rotated to move a container 100 that includes reagent vessels 116 to 118 to the dispensing/stirring position 113 located on the outer disk 110. The reagent vessel 116 contains a magnetic-particle reagent to be dispensed in the current cycle. Hereinafter, the above container 100 that has been placed at the dispensing/stirring position 113 located on the outer disk 110 during Step S103 is instead referred to as the container (N1). The magnetic-particle reagent of the reagent vessel 116 inside the container (N1) has already been stirred during the previous cycle before the current one.

<Step S104>

The control device controls the device for opening/closing the lids of reagent 121 to simultaneously open the lid 101a of the reagent vessel 116 inside the container (N+1) placed on the inner disk 111 and at least one of the lids 101d to 101f of the reagent vessels 116 to 118 inside the container (N1) placed on the outer disk 110. Because one reagent or two reagents are dispensed at a time, one or two of the reagent vessels 116 to 118 inside the container (N1) are opened during Step S104.

<Step S105>

The reagent stirring rod 109 is put in the opened reagent vessel 116 inside the container (N+1) to stir the magnetic-particle reagent as long as possible (i.e., until the reagent is dispensed during the next cycle) so that the reagent will not precipitate.

<Step S106>

Step S106 starts at substantially the same time as Step S105. During Step S106, one or two of the reagent suctioning probes 108 are put in the opened reagent vessel(s) inside the container (N1) for reagent dispensation.

<Step S107>

The device for opening/closing the lids of reagent vessels 121 closes the reagent vessel(s) inside the container (N1) for which the dispensing operation by the reagent suctioning probe(s) 108 has been completed. At this point, the stirring operation still continues inside the container (N+1); therefore, the lid closing operation is performed on the container (N1) only, with the lid 101a of the reagent vessel 116 inside the container (N+1) being kept open.

<Step S108>

The outer disk 110 is rotated to move the container (N1) out of the dispensing/stirring position 113 on the outer disk 110 and move another container 100 that includes reagent vessels 116 to 118 to the dispensing/stirring position 113 on the outer disk 110. The reagent vessel 117 included in this container 100 contains a reagent A, or the reagent vessel 118 in the container 100 contains a reagent B (or both the reagent vessels 117 and 118 contain the reagents A and B, respectively). The reagents A and B are to be dispensed during the current cycle. Hereinafter, the above container 100 that has been placed at the dispensing/stirring position 113 located on the outer disk 110 during Step S108 is instead referred to as the container (N2).

<Step S109>

The control device controls the device for opening/closing the lids of reagent 121 to open the lid 101e of the reagent vessel 117 or the lid 101f of the reagent vessel 118 (or both) inside the container (N2) located on the outer disk 110, with the lid 101a of the reagent vessel 116 inside the container (N+1) on the inner disk 111 being kept open.

<Step S110>

One or two of the reagent suctioning probes 108 are put in the opened reagent vessel(s) inside the container (N2) for reagent dispensation, as in Step S106. The completion of the dispensing operation of Step S110 is simultaneous with or shortly before or after the completion of the stirring operation of Step S105.

<Step S111>

The control device controls the device for opening/closing the lids of reagent vessels 121 to simultaneously close the lid 101a of the reagent vessel 116 inside the container (N+1) located on the inner disk 111 and the lid 101e of the reagent vessel 117 or the lid 101f of the reagent vessel 118 (or both) inside the container (N2) located on the outer disk 110.

<Step S112>

The reagent transfer mechanism (not illustrated) moves the container (N+1), for which the stirring operation of the current cycle has been completed, to the dispensing/stirring position 113 on the outer disk 110.

By repeating the above operational sequence, a series of analyses proceed.

It should be noted that, in the flowchart of FIG. 13, the container (N1) and the container (N2) can be switched in the order of reagent dispensation. In that case, the rest of the operational sequence is the same, except the switched order of reagent dispensation.

As stated above, the device for opening/closing the lids of reagent vessels 121 of the present embodiment is capable of selectively opening or closing the lids 101a to 101f of reagent vessels 116 to 118. This selective lid opening or closing is achieved by 1) attaching the multiple hooks 102a to 102f to the hook base 104, 2) providing hook drive mechanisms (not illustrated) inside the hook base 104 to individually engage/disengage the hooks 102a to 102f with/from the lids 101a to 101f, and 3) moving the hook base 104 in opening/closing directions of the lids 101a to 101f with the use of the hook-base drive unit 106.

Therefore, when opening a particular reagent vessel, the device for opening/closing the lids of reagent vessels 121 opens only that vessel without opening other reagent vessels. Moreover, even when a dispensing operation is completed before a stirring operation or vice versa, the device for opening/closing the lids of reagent vessels 121 can immediately close reagent vessels that need to be closed each time the dispensing or stirring operation is completed. Thus, the present embodiment can reduce the time period during which reagent vessels are opened unnecessarily.

A possible alternative method for selectively opening or closing reagent vessels is to prepare a motor for each of the lids 101a to 101f of reagent vessels 116 to 118 and make the motors connect/disconnect their output shafts to/from the shafts of the lids 101a to 101f. This method, however, is not desirable. Because a relatively large torque is required for the motor to open or close each of the lids 101a to 101f, it is not desirable for the automated analyzer to have those multiple motors each with such a large torque. Besides, connecting/disconnecting the shafts of the lids 101a to 101f to/from the output shafts of the motors requires to provide a special device on a side of the regent vessels 116 to 118 for that purpose, which device takes a larger installation space in a reagent disk.

The device for opening/closing the lids of reagent vessels 121 of the present embodiment, in contrast, uses the hooks 102a to 102f to hook the lids 101a to 101f from above and moves the hook base 104 upward or downward to open or close the lids 101a to 101f. Thus, the device for opening/closing the lids of reagent vessels 121 takes a smaller installation space. Moreover, for lid opening/closing, the device for opening/closing the lids of reagent vessels 121 is provided with the hook-base drive unit 106 and hook drive mechanisms (not illustrated), which mechanisms require only a small rotational force to rotate the hooks 102a to 102f. Thus, motors with a large torque are not necessary.

The device for opening/closing the lids of reagent vessels 121 is also capable of adjusting the force of the hook base 104 to press the lids 101a to 101f of reagent vessels 116 to 118 downward during lid closing, by adjusting the operation (i.e., rotational angle) of the hook-base drive unit 106. Therefore, the device for opening/closing the lids of reagent vessels 121 is capable of partially closing the lids 101a to 101f without closing them completely, as illustrated in FIGS. 14 through 22. FIGS. 14 to 22 correspond to FIGS. 4 to 12, and the same operations as in FIGS. 4 to 12 can be performed for closing the lids 101a to 101f partially. FIGS. 14 to 22 are basically the same as FIGS. 4 to 12 except that in FIGS. 14 to 22, the rotational angle of the hook-base drive unit 106 is changed.

The partial lid closure of FIGS. 14 to 22 requires a smaller force in opening or closing the lids 101a to 101f than in FIGS. 4 to 12. The partial lid closure is also advantageous in that the upward/downward movement of the hook base 104 takes less time due to the reduced rotational angle of the hook-base drive unit 106.

However, due to a reduction in the air tightness of reagent vessels, the partial lid closure may result in gradual reagent evaporation or deterioration when the partial closure lasts for a long amount of time. One of the cases where the partial lid closure of FIGS. 14 to 22 is applicable is the one below.

As is often the case with automated analyzers in general, the automated analyzer of the present embodiment receives, before an analysis, the input of request information on attributes to be analyzed, analysis order, the number of samples, and the like and is capable of creating schedule information such as when to use reagents and how many times they are used. Thus, a control device (not illustrated) of the automated analyzer refers to the schedule information based on the request information after opening the lid 101 of a particular reagent vessel with the use of the device for opening/closing the lids of reagent vessels 121. Upon lid closure, the control device instructs the device for opening/closing the lids of reagent vessels 121 to partially close the lid 101 of that reagent vessel when the reagent vessel is to be used later again or completely close the lid 101 of the reagent vessel when the reagent vessel is no longer to be used. When the reagent vessel is used again, the control device recognizes the partially closed state of the reagent vessel based on the schedule information and automatically adjusts the operation of the hook-base drive unit 106. To summarize the above, during a series of analyses, the control device exercises control as so to partially close the lid of a particular reagent vessel during the time interval between its first use and last use and completely close the lid of the reagent vessel after the last use. Thus, the device for opening/closing the lids of reagent vessels 121 is capable of automatically close the lids 101 of all reagent vessels completely after the end of the operation of the automated analyzer, while reducing the time to open or close the lids 101 to improve processing efficiency and reducing the force necessary to open or close the lids 101. The complete lid closure prevents reagent evaporation or deterioration even when reagent vessels are left untouched overnight or for several days.

It the above-described embodiment, the lids 101a to 101f of reagent vessels 116 to 118 move around the inner-disk-side fulcrums of the reagent vessels 116 to 118 in a plane that includes the rotational axis of the reagent disk 120, and the hook base 104 of the device for opening/closing the lids of reagent vessels 121 moves in a similar manner. When the postures of the shafts of the lids 101a to 101f at the dispensing/stirring position 113 are to be changed, however, the movement of the hook base 104 also needs to be changed accordingly. The movement of the hook base 104 is not limited to particular movements as long as the hook base 104 and the lids 101a to 101f move in a similar manner. The postures and movement directions of the hooks 102a to 102f are also subject to change when changes are made to the structures of the lids 101a to 101f (e.g., the structures of portions to be hooked) or their shaft postures.

As stated above, the automated analyzer of the invention stores dozens of reagent vessel sets inside the reagent disk 120 that is surrounded by the reagent refrigerator 115 and transfers particular vessel sets at the dispensing/stirring position 113 at which the particular vessel sets are opened or closed and accessed by the reagent suctioning probes 108 and the reagent stirring rod 109. However, the automated analyzer can instead be allowed to transfer the device for opening/closing the lids of reagent vessels 121 having the reagent suctioning probes 108 and the reagent stirring rod 109 to particular vessel sets without moving any reagent vessel set (in this case, the transfer destination becomes the dispensing/stirring position 113).

The aforementioned can be applied to, for example, the standby position 112 instead of dispensing/stirring position 113. Alternatively, the reagent suctioning probes 108, the reagent stirring rod 109 and the device for opening/closing the lids of reagent vessels 121 are additionally provided near the standby position 112, so that the opening or closing the lids of the reagent vessels, suctioning or dispensing the reagent and stirring the magnetic particles can be carried out, for the reagent vessels 100 positioned at the standby position 112. Thereby, the standby position 112 can be used not only for analyzing but also for stocking the reagent vessels. This modification is effective in the case where the reagent is sensitive to the motion and tends to deteriorate due to the motion. Even if such modification cannot be made, it is possible to reduce the movement of the reagent vessel by using a portion of the standby position 112 as a stock position for the reagent vessel including the reagent sensitive to the motion. In this case, the reagent vessel is transferred to the outer disk 110 and to the dispensing/stirring position 113 only when the sensitive reagent is to be analyzed, and immediately after the analyzing is carried out, the reagent vessel is returned to the standby position 112 to be stocked at the standby position 112.

The invention claimed is:

1. A reagent vessel holding device for placing thereon a plurality of sets of reagent vessels, each of the sets including a plurality of reagent vessels, and each of the reagent vessels including a reagent to be used for analysis of a sample, comprising:
   a holding member for holding thereon the plurality of sets of reagent vessels; and
   a reagent vessel opening/closing device to open or close a lid of at least one of the reagent vessels in one of the sets when the one of the sets is at a dispensing/stirring position on the reagent vessel holding device, wherein the reagent vessel opening/closing device includes:
   a unit base arranged on the holding member;
   a hook base secured to the unit base;

a hook-base drive unit which moves the hook base with respect to the unit base in opening/closing directions of the lids of the reagent vessels in the one of the sets;

a plurality of hooks attached to the hook base; and a plurality of hook drive units, each of the hook drive units configured to drive a respective one of the hooks to move independently of the other hooks on the hook base to engage/disengage the respective one of the hooks with/from the lid of a corresponding one of the reagent vessels in the one of the sets.

2. The reagent vessel holding device of claim 1, wherein to open at least one of the reagent vessels in the one of the sets, the reagent vessel opening/closing device places the respective one of the hooks in an engagement position with the hook base located at a lower position and then moves the hook base in an opening direction of the lid of the at least one of the reagent vessels in the one of the sets with the hook-base drive unit so that the respective hook can lift the lid thereof, and wherein to close at least one of the reagent vessels in the one of the sets, the reagent vessel opening/closing device moves the hook base in a closing direction of the lid of the at least one of the reagent vessels in the one of the sets with the hook-base drive unit with the respective one of the hooks placed in an engagement position so that the respective hook presses the lid thereof downward.

3. The reagent vessel holding device of claim 2, wherein to move the hook base in the closing direction while keeping a lid of another of the reagent vessels in the one of the sets open, the reagent vessel opening/closing device places the respective hook associated with the other of the reagent vessels to be kept open in a disengagement position with the hook base moved in a closing direction of the lid of the one of the reagent vessels in the one of the sets to be closed with the hook-base drive unit.

4. The reagent vessel holding device of claim 2, wherein the hook-base drive unit is adjustable so as to control a force with which the lid of the one of the reagent vessels in the one of the sets is pressed downward.

5. The reagent vessel holding device of claim 1, further comprising:

a control device for controlling the hook-base drive unit and the hook drive units based on analysis request information for a reagent held on the holding member, so that the lids of reagent vessels can be opened during reagent dispensing operations and reagent stirring operations, and can be closed after the completion of each of the dispensing operations and each of the stirring operations.

6. A reagent vessel opening/closing device for opening or closing a lid of at least one of a plurality of reagent vessels when the reagent vessels lie at a dispensing/stirring position, comprising:

a unit base;

a hook base secured to the unit base;

a hook-base drive unit which moves the hook base with respect to the unit base in opening/closing directions of the lids of the reagent vessels;

a plurality of hooks attached to the hook base; and a plurality of motors, each of the motors configured to drive a respective one of the hooks to move independently of the other hooks on the hook base to engage/disengage the respective one of the hooks with/from the lid of a corresponding one of the reagent vessels.

7. The reagent vessel holding device of claim 3, wherein the hook-base drive unit is adjustable so as to control a force with which to press the lid of the corresponding one of the reagent vessels downward.

8. The reagent vessel holding device of claim 2, further comprising:

a control device for controlling the hook-base drive unit and the hook drive units based on analysis request information for a reagent held on the holding member, so that the lids of reagent vessels can be opened during reagent dispensing operations and reagent stirring operations, and can be closed after the completion of each of the dispensing operations and each of the stirring operations.

9. The reagent vessel holding device of claim 3, further comprising:

a control device for controlling the hook-base drive unit and the hook drive units based on analysis request information for a reagent held on the holding member, so that the lids of reagent vessels can be opened during reagent dispensing operations and reagent stirring operations, and can be closed after the completion of each of the dispensing operations and each of the stirring operations.

10. The reagent vessel holding device of claim 4, further comprising:

a control device for controlling the hook-base drive unit and the hook drive units based on analysis request information for a reagent held on the holding member, so that the lids of reagent vessels can be opened during reagent dispensing operations and reagent stirring operations, and can be closed after the completion of each of the dispensing operations and each of the stirring operations.

* * * * *